United States Patent [19]

Donahoe et al.

[11] Patent Number: 5,547,854

[45] Date of Patent: Aug. 20, 1996

[54] DNA ENCODING A RECEPTOR FOR MÜLLERIAN INHIBITORY SUBSTANCE, MISR1, AND CORRESPONDING VECTORS, CELLS, PROBES, AND RECOMBINANT METHODS

[75] Inventors: Patricia K. Donahoe, Weston; Michael Gustafson, Boston, both of Mass.; Wei W. He, Germantown, Md.

[73] Assignee: The General Hospital Corporation, Boston, Mass.

[21] Appl. No.: 317,847

[22] Filed: Oct. 4, 1994

Related U.S. Application Data

[63] Continuation of Ser. No. 29,673, Mar. 11, 1993, abandoned, which is a continuation-in-part of Ser. No. 853,396, Mar. 18, 1992, abandoned.

[51] Int. Cl.$^6$ .......................... C12N 15/12; C12N 15/63; C12N 5/10; C07K 14/715
[52] U.S. Cl. ................ 435/69.1; 536/23.5; 536/24.31; 536/24.33; 435/320.1; 435/240.2; 435/252.3; 435/254.11; 530/351
[58] Field of Search .................... 536/23.5, 24.31, 536/24.33; 435/69.1, 320.1, 240.2, 252.3, 254.11

[56] References Cited

U.S. PATENT DOCUMENTS

| | | | |
|---|---|---|---|
| 4,404,188 | 9/1983 | Donahoe et al. | 424/105 |
| 4,487,833 | 12/1984 | Donahoe et al. | 435/172.2 |
| 4,510,131 | 4/1985 | Donahoe et al. | 424/105 |
| 4,753,794 | 6/1988 | Donahoe | 424/85 |
| 4,792,601 | 12/1988 | Donahoe et al. | 530/387 |
| 5,010,055 | 4/1991 | Donahoe | 514/8 |
| 5,011,687 | 4/1991 | Donahoe et al. | 424/559 |
| 5,047,336 | 9/1991 | Cate et al. | 435/69.4 |

FOREIGN PATENT DOCUMENTS

PCT/US93/ 02387 6/1993 WIPO.

OTHER PUBLICATIONS

Young et al., Proceedings of the National Academy of Sciences of the USA, vol. 80, Issued Mar. 1983, pp. 1194–1198.
Suggs et al., Proceedings of the National Academy of Sciences of the USA, vol. 78, No. 11, pp. 6613–6617.
Matsuzaki et al., Genbank Record No. L02911, Sep. 29, 1992.
Abe et al., J. Clinical Endocrinology and Metabolism 71:133–137, 1990.
Au et al., Biology of Reproduction 35:37–43, 1986.
Behringer et al., Nature 345:167–170, 1990.
Berta et al., Nature 348:448–450, 1990.
Bezard et al., Reprod. Fert. 80:509–516, 1987.
Blanchard and Josso, Pediat. Res. 8:968–971, 1974.
Budzik et al., Cell 21:909–916, 1980.
Budzik et al., Cell 34:307–314, 1983.
Burger et al., J. Clinical Endocrinology and Metabolism 67:689–694, 1988.
Cate et al., Cold Spring Harbor Symposium 51:641–647, 1986.
Cate et al., Cell 45:685–698, 1986.
Catlin et al, Am. Rev. Respir. Dis. 141:466–470, 1990.
Catlin et al., Am. J. Obstet. Gynecol. 159:1299–303, 1988.
Chin et al., Cancer Research 51:2101–2106, 1991.
Cohen–Maguenauer et al., Cytogenet. Cell Genet. 44:2–6, 1987.
Coughlin et al., Molecular and Cellular Endocrinology 49:75–86, 1987.
de Kretser et al., J. of Endocrinology 120:517–523, 1989.
de Kretser et al., Biology of Reproduction 40:33–47, 1989.
Deryrck et al., Nature 316:701–705, 1985.
Donahoe et al., Science 205:913–915, 1979.
Donahoe et al., Ovarian Cancer 194:472–480, 1981.
Donahoe et al., Biology of Reproduction 16:238–243, 1977.
Epstein et al., In Vitro Cellular and Developmental Biology 25:213–216, 1989.
Esch et al., Molecular Endocrinology 1:388396, 1987.
Forage et al., Proc. Natl. Acad. Sci. USA 83:3091–3095, 1986.
Fuller et al., Gynocologic Oncology 22:135–148, 1985.
Fuller et al., Gynecology Oncology 17:124–132, 1984.
Fuller·et al., J. Clinical Endocrinology and Metabolism 54:1051–1055, 1982.
Georgi et al., Cell 61:635–645, 1990.
Gubbay et al, Nature 346:245–250, 1990.
Gustafson et al., New England Journal of Medicine 326:466–471, 1992.
Hagg et al., Genomics 12:665–669, 1992.
Hasegawa et al., J. Endocrinology 121:91–100, 1989.
Hsueh et al., Proc. Natl. Acad. Sci. USA 84:5082–5086, 1987.
Hudson et al., J. Clinical Endocrinology and Metabolism 70:16–22, 1990.
Hutson and Donahoe, Endocrine Reviews 7:270–283, 1986.
Josso et al., J. Clinical Endocrinology and Metabolism 70:23–27, 1990.
King et al., Genomics 11:273–283, 1991.
Knebelmenn et la., Proc. Natl. Acad. Sci. USA 88:3767–3771, 1991.
Lappohn et al., The New England Journal of Medicine 321:790–793, 1989.
Lin et al., Cell 68:775–785, 1992.
Ling et al., Nature 321:779–782, 1986.

(List continued on next page.)

*Primary Examiner*—Stephen G. Walsh
*Assistant Examiner*—David L. Fitzgerald
*Attorney, Agent, or Firm*—Fish & Richardson, P.C.

[57] ABSTRACT

Isolated DNAs (e.g., cDNAs or genomic fragments) encoding MIS receptors, inhibin receptors, bone morphogenic protein receptors, or other novel members of the TGF-β family of receptors, or soluble, ligand-binding fragments thereof; vectors or cells which contain such DNAs; and substantially pure polypeptides encoded by such DNAs, whether produced by expression of the isolated DNAs, by isolation from natural sources, or by chemical synthesis.

27 Claims, 13 Drawing Sheets

OTHER PUBLICATIONS

MacLaughlin et al., Methods in Enzymology 198:358–369, 1991.

Mason et al., Nature 318:659–663, 1985.

Mason et al., Biochemical and Biophysical Research Communications 135:957–964, 1986.

Mathews and Vale, Cell 65:973–982, 1991.

Mayo et al., Proc. Natl. Acad. Sci. USA 83:5849–5853, 1986.

McCullagh, Science 70:19–20, 1932.

McLachlan et al., Molecular and Cellular Endocrinology 46:175–185, 1986.

McLachlan et al., J. Clin. Invest. 82:880–884, 1988.

McLachlan et al., J. of Clinical Endocrinology and Metabolism 65:954–961, 1987.

Neunier et al., Proc. Natl. Acad. Sci. USA 85:247–251, 1988.

Miyamoto et al., Biochemical and Biophysical Research Communications 136:1103–1109, 1986.

Munsterberg and Lovell–Badge, Development 113:613–624, 1991.

Padgett et al., Nature 325:81–84, 1987.

Petraglia et al., Science 237:187–189, 1987.

Picard and Josso, Molecular and Cellular Endocrinology 34:23–29, 1984.

Schneyer et al., J. Clinical Endocrinology and Metabolism 70:1208–1212, 1990.

Sheckter et al., J. Clinical Endocrinology and Metabolism 67:1221–1224, 1988.

Sinclair et al., Nature 346:240–244, 1990.

Takahashi et al., Molecular and Cellular Endocrinology 47:225–234, 1986.

Takahashi et al., Biology of Reproduction 35:447–453, 1986.

Taketo et al., Developmental Biology 166:386–395, 1991.

Ueno et al., Endocrinology 124:1000–1006, 1989.

Ueno et al., Endocrinology 123:1652–1659, 1988.

Ueno et al., Endocrinology 125:1060–1066, 1989.

Vale et al., Recent Progress in Hormone Research 44:1–34, 1988.

Vale et al., Nature 321:776–779, 1986.

Vigier et al., Proc. Natl. Acad. Sci. USA 86:3684–3688, 1989.

Vigier et al., Development 100:43–45, 1987.

Weeks and Melton, Cell 51:861–867, 1987.

Woodruff et al., Endocrinology 127:3196–3205, 1990.

Woodruff et al., Science 239:1296–1299, 1988.

Wozney et al., Science 242:1528–1534, 1988.

Tsuchida, K., et al., *Proc. Natl. Acad. Sci. USA* 90: 11242–46, 1993.

Nowak, R., *Science* 262: 1818, 1993.

Lefévre, G., et al., *Mol. Cell. Endocrinol.* 62: 125–33, 1989.

Teng C. S., et al., *J. Cell Biol.* 107 (6, pt. 3): p. 71A, abstract 381, 1988.

Siu, G., et al., *J. Exp. Med.* 164: 1600–14, 1986.

```
                560                  580                  600
atggtcgatggagcaatgatcctttctgtgctaatgatgatggctctcccttccccgagt
MetValAspGlyAlaMetIleLeuSerValLeuMetMetMetAlaLeuProSerProSer
                620                  640                  660
atggaagatgaggagcccaaggtcaacccgaagctttacatgtgtgtgtgtgagggcctc
MetGluAspGluGluProLysValAsnProLysLeuTyrMetCysValCysGluGlyLeu
                680                  700                  720
tcctgcgggaacgaggaccactgtgagggccagcagtgttttcctccctgagcgtcaat
SerCysGlyAsnGluAspHisCysGluGlyGlnGlnCysPheSerSerLeuSerValAsn
                740                  760                  780
gatggcttccgcgtctaccagaagggctgctttcaggtctatgagcaggggaagatgacg
AspGlyPheArgValTyrGlnLysGlyCysPheGlnValTyrGluGlnGlyLysMetThr
                800                  820                  840
tgtaagaccccgccgtcgcctggccaggctgtggagtgctgccaaggggactggtgcaac
CysLysThrProProSerProGlyGlnAlaValGluCysCysGlnGlyAspTrpCysAsn
                860                  880                  900
aggaacgtcacggcccggctgcccactaaagggaaatccttccctggatcgcagaacttc
ArgAsnValThrAlaArgLeuProThrLysGlyLysSerPheProGlySerGlnAsnPhe
                920                  940                  960
cacctggaagttggcctTatcatcctctccgtggtgtttgcggtatgccttttcgcttgc
HisLeuGluValGlyLeuIleIleLeuSerValValPheAlaValCysLeuPheAlaCys
                980                 1000                 1020
atccttggcgttgctctcaggaagtttaaaaggcgcaatcaagagcgcctgaaccccaga
IleLeuGlyValAlaLeuArgLysPheLysArgArgAsnGlnGluArgLeuAsnProArg
               1040                 1060                 1080
gacgtggagtacggtactatcgaagggctcatcaccaccaacgtcggagatagcactcta
AspValGluTyrGlyThrIleGluGlyLeuIleThrThrAsnValGlyAspSerThrLeu
               1100                 1120                 1140
gcggaattactagatcactcgtgtacatcaggaagtggctccggtcttccttttctggta
AlaGluLeuLeuAspHisSerCysThrSerGlySerGlySerGlyLeuProPheLeuVal
               1160                 1180                 1200
cagagaactgtggctcgacagataaccctgttggagtgtgtcgggaagggccggtatgga
GlnArgThrValAlaArgGlnIleThrLeuLeuGluCysValGlyLysGlyArgTyrGly
               1220                 1240                 1260
gaagtgtggaggggcagctggcaaggcgaaaatgttgctgtgaagatcttctcctcccgt
GluValTrpArgGlySerTrpGlnGlyGluAsnValAlaValLysIlePheSerSerArg
               1280                 1300                 1320
gatgagaagtcgtggttcagggagacagaattgtacaacacggtgatgctgaggcatgag
AspGluLysSerTrpPheArgGluThrGluLeuTyrAsnThrValMetLeuArgHisGlu
               1340                 1360                 1380
aatatcttaggtttcattgcttcagacatgacctctagacactccagtacccagctgtgg
AsnIleLeuGlyPheIleAlaSerAspMetThrSerArgHisSerSerThrGlnLeuTrp
               1400                 1420                 1440
ctcattacacattaccacgaaatgggatcgttgtatgactaccttcagctcaccactctg
LeuIleThrHisTyrHisGluMetGlySerLeuTyrAspTyrLeuGlnLeuThrThrLeu
               1460                 1480                 1500
gacacggttagctgccttcggatcgtgttgtccatagccagcggccttgcacacttgcac
AspThrValSerCysLeuArgIleValLeuSerIleAlaSerGlyLeuAlaHisLeuHis
```

FIG. 1a

```
              1520                1540                1560
  atagagatatttgggacccaggggaagtctgccatcgcccaccgagatctaaagagcaaa
  IleGluIlePheGlyThrGlnGlyLysSerAlaIleAlaHisArgAspLeuLysSerLys
              1580                1600                1620
  aacatcctcgtgaagaagaacggacagtgctgcatagcagatttgggcctggcagtcatg
  AsnIleLeuValLysLysAsnGlyGlnCysCysIleAlaAspLeuGlyLeuAlaValMet
              1640                1660                1680
  cattcccagagcacgaatcagcttgatgtgggaaacaacccccgtgtggggaccaagcgc
  HisSerGlnSerThrAsnGlnLeuAspValGlyAsnAsnProArgValGlyThrLysArg
              1700                1720                1740
  tacatggcccctgaagtgcttgatgaaaccatccaagtggattgctttgattcttataag
  TyrMetAlaProGluValLeuAspGluThrIleGlnValAspCysPheAspSerTyrLys
              1760                1780                1800
  agggtcgatatttgggcctttggcctcgttctgtgggaagtggccaggaggatggtgagc
  ArgValAspIleTrpAlaPheGlyLeuValLeuTrpGluValAlaArgArgMetValSer
              1820                1840                1860
  aatggtatagtggaagattacaagccaccattctatgatgttgttcccaatgacccaagt
  AsnGlyIleValGluAspTyrLysProProPheTyrAspValValProAsnAspProSer
              1880                1900                1920
  tttgaagatatgaggaaagttgtctgtgtggatcaacagaggccaaacatacctaacaga
  PheGluAspMetArgLysValValCysValAspGlnGlnArgProAsnIleProAsnArg
              1940                1960                1980
  tggttctcagacccgacattaacttctctggcgaagctgatgaaagaatgctggtaccag
  TrpPheSerAspProThrLeuThrSerLeuAlaLysLeuMetLysGluCysTrpTyrGln
              2000                2020                2040
  aacccatccgccagactcacagctctacgtatcaaaaagactttgaccaaaattgataac
  AsnProSerAlaArgLeuThrAlaLeuArgIleLysLysThrLeuThrLysIleAspAsn
              2060
  tccctagacaaattaaaaactgactgttga
  SerLeuAspLysLeuLysThrAspCysEnd
```

FIG. 1b

```
         10                  30                  50
atggcggagtcggccggagcctcctccttcttccccttgttgtcctcctgctcgccggc
MetAlaGluSerAlaGlyAlaSerSerPhePheProLeuValValLeuLeuLeuAlaGly
         70                  90                 110
agtggcgggtccgggccccggggggatccaggctctgctgtgtgcatgcaccagctgccta
SerGlyGlySerGlyProArgGlyIleGlnAlaLeuLeuCysAlaCysThrSerCysLeu
        130                 150                 170
cagaccaactacacctgcgaaacagatggggcctgcatggtctccatctttaacctggat
GlnThrAsnTyrThrCysGluThrAspGlyAlaCysMetValSerIlePheAsnLeuAsp
        190                 210                 230
ggcatggagcaccacgtacgcacctgcatccccaaggtggagcttgtgcctgctgggaag
GlyMetGluHisHisValArgThrCysIleProLysValGluLeuValProAlaGlyLys
        250                 270                 290
cccttctactgcctgagttcagaggacctgcgcaacacgcactgctgctatattgacttc
ProPheTyrCysLeuSerSerGluAspLeuArgAsnThrHisCysCysTyrIleAspPhe
        310                 330                 350
tgcaacaagattgacctgagggtgcccagtggacacctcaaggagcctgagcaccctcc
CysAsnLysIleAspLeuArgValProSerGlyHisLeuLysGluProGluHisProSer
        370                 390                 410
atgtggggccctgtggagctggtcggcatcattgccggtcctgtcttcctcctcttcctc
MetTrpGlyProValGluLeuValGlyIleIleAlaGlyProValPheLeuLeuPheLeu
        430                 450                 470
atcatcatcatcgtcttcctggtcatcaactatcatcagcgtgtctaccacaaccgccaa
IleIleIleIleValPheLeuValIleAsnTyrHisGlnArgValTyrHisAsnArgGln
        490                 510                 530
agactggacatggaggaccctcatgtgagatgtgtctctccaaagacaagacgctccag
ArgLeuAspMetGluAspProSerCysGluMetCysLeuSerLysAspLysThrLeuGln
        550                 570                 590
gatctcgtctacgatctctccacttcaggatcgggctcagggttaccccttttgtccag
AspLeuValTyrAspLeuSerThrSerGlySerGlySerGlyLeuProLeuPheValGln
        610                 630                 650
cgcacagtggcccgaaccattgttttacaagagattatcggcaagggccggtttggggaa
ArgThrValAlaArgThrIleValLeuGlnGluIleIleGlyLysGlyArgPheGlyGlu
        670                 690                 710
gtatggcgtggccgctggaggggtggtgatgtggctgtgaaaatcttctcttcccgtgaa
ValTrpArgGlyArgTrpArgGlyGlyAspValAlaValLysIlePheSerSerArgGlu
        730                 750                 770
gagcggtcgtggttccgggaggcagagatctaccagactgtcatgctgcgccatgaaaac
GluArgSerTrpPheArgGluAlaGluIleTyrGlnThrValMetLeuArgHisGluAsn
        790                 810                 830
atccttgggtttattgctgctgacaataaagacaatggcacctggacccagctgtggctt
IleLeuGlyPheIleAlaAlaAspAsnLysAspAsnGlyThrTrpThrGlnLeuTrpLeu
        850                 870                 890
gtctctgactatacgagcacggctcactgttcgattatctgaaccgctacacagtgacc
ValSerAspTyrHisGluHisGlySerLeuPheAspTyrLeuAsnArgTyrThrValThr
        910                 930                 950
attgaggggatgattaaactggccctgtctgcagccagtggtttggcacacctgcatatg
IleGluGlyMetIleLysLeuAlaLeuSerAlaAlaSerGlyLeuAlaHisLeuHisMet
```

FIG. 2a

```
             970                 990                 1010
    gagattgtgggcactcaggggaagcctggaattgctcatcgagacttgaagtcaaagaac
    GluIleValGlyThrGlnGlyLysProGlyIleAlaHisArgAspLeuLysSerLysAsn
             1030                1050                1070
    attctggtgaagaagaatggcatgtgtgccattgcagacctgggcctagctgtccgtcac
    IleLeuValLysLysAsnGlyMetCysAlaIleAlaAspLeuGlyLeuAlaValArgHis
             1090                1110                1130
    gatgctgtcactgacaccatagacattgctccaaatcagagggtgggaaccaaacgatac
    AspAlaValThrAspThrIleAspIleAlaProAsnGlnArgValGlyThrLysArgTyr
             1150                1170                1190
    atggctcctgaagtacttgacgagaccatcaacatgaagcactttgactccttcaagtgt
    MetAlaProGluValLeuAspGluThrIleAsnMetLysHisPheAspSerPheLysCys
             1210                1230                1250
    gccgatatctacgccctcgggcttgtctattgggagattgctcggaggtgcaattctgga
    AlaAspIleTyrAlaLeuGlyLeuValTyrTrpGluIleAlaArgArgCysAsnSerGly
             1270                1290                1310
    ggagtccatgaagagtatcaactgccatattatgatttagtgccctctgacccttccatt
    GlyValHisGluGluTyrGlnLeuProTyrTyrAspLeuValProSerAspProSerIle
             1330                1350                1370
    gaggaaatgcgaaaggtcgtctgtgaccagaagctacggcccaatgtccccaactggtgg
    GluGluMetArgLysValValCysAspGlnLysLeuArgProAsnValProAsnTrpTrp
             1390                1410                1430
    cagagttatgaggccttgcgagtgatggggaagatgatgcgggagtgctggtacgccaat
    GlnSerTyrGluAlaLeuArgValMetGlyLysMetMetArgGluCysTrpTyrAlaAsn
             1450                1470                1490
    ggtgctgcccgcctgacagcgctgcgcatcaagaagactttgtcccagctaagcgtgcag
    GlyAlaAlaArgLeuThrAlaLeuArgIleLysLysThrLeuSerGlnLeuSerValGln
             1510
    gaagacgtgaagatttaa
    GluAspValLysIleEnd
```

FIG. 2b

```
            270                 290                  310
atgaccctggggattttcgaagggtcttttgatgctgtcggtggccttgggcctaact
MetThrLeuGlyIlePheArgArgValPheLeuMetLeuSerValAlaLeuGlyLeuThr
            330                 350                  370
aagggagacttggtgaagccctccagggtcagctggtaaactgcacttgtgagaaccca
LysGlyAspLeuValLysProSerArgGlyGlnLeuValAsnCysThrCysGluAsnPro
            390                 410                  430
cactgcaagaggccaatctgccaggggcatggtgcacagtggtgctagttcgagagcag
HisCysLysArgProIleCysGlnGlyAlaTrpCysThrValValLeuValArgGluGln
            450                 470                  490
ggcaggcaccccaggtctatcggggctgcgggagcctgaaccaggagctctgcctggga
GlyArgHisProGlnValTyrArgGlyCysGlySerLeuAsnGlnGluLeuCysLeuGly
            510                 530                  550
cgtcccacggagtttgtgaaccatcactgctgctatagatccttctgcaaccacaatgtg
ArgProThrGluPheValAsnHisHisCysCysTyrArgSerPheCysAsnHisAsnVal
            570                 590                  610
tccctgatgctggaggccacccaaactccttcggaggagccagaagtagatgcccatctg
SerLeuMetLeuGluAlaThrGlnThrProSerGluGluProGluValAspAlaHisLeu
            630                 650                  670
cctctgatcctgggtcccgtgctggccttgctggtcctggtggccctgggcactctgggc
ProLeuIleLeuGlyProValLeuAlaLeuLeuValLeuValAlaLeuGlyThrLeuGly
            690                 710                  730
ttgtggcgtgtccggagaaggcaggagaagcagcggggtctgcacagtgacctgggcgag
LeuTrpArgValArgArgArgGlnGluLysGlnArgGlyLeuHisSerAspLeuGlyGlu
            750                 770                  790
tccagtctcatcctgaaggcatcggaacagggagacagcatgttgggggacttcctggtc
SerSerLeuIleLeuLysAlaSerGluGlnGlyAspSerMetLeuGlyAspPheLeuVal
            810                 830                  850
agcgactgtaccacaggcagcggctcagggctacccttcttggtgcagaggacagtagcg
SerAspCysThrThrGlySerGlySerGlyLeuProPheLeuValGlnArgThrValAla
            870                 890                  910
cgacaggttgcactggtggagtgtgtgggaaagggccgatatggcgaggtgtggcgcggt
ArgGlnValAlaLeuValGluCysValGlyLysGlyArgTyrGlyGluValTrpArgGly
            930                 950                  970
tcgtggcatggcgagagtgtggcggtcaagatttctcctcacgagatgagcagtcctgg
SerTrpHisGlyGluSerValAlaValLysIlePheSerSerArgAspGluGlnSerTrp
            990                1010                 1030
ttccgggagacagagatctacaacacagttctgcttagacacgacaacatcctaggcttc
PheArgGluThrGluIleTyrAsnThrValLeuLeuArgHisAspAsnIleLeuGlyPhe
           1050                1070                 1090
atcgcctccgacatgacctcgcggaactccagcacgcagctgtggcttatcacccactac
IleAlaSerAspMetThrSerArgAsnSerSerThrGlnLeuTrpLeuIleThrHisTyr
           1110                1130                 1150
cacgagcatggctccctctatgactttctgcagaggcagacgctggagccccagttggcc
HisGluHisGlySerLeuTyrAspPheLeuGlnArgGlnThrLeuGluProGlnLeuAla
```

FIG. 3a

```
            1170              1190              1210
ctgaggctggctgtgtccgcggcctgcgctggcctggcgcacctgcatgtagagatcttt
LeuArgLeuAlaValSerAlaAlaCysAlaGlyLeuAlaHisLeuHisValGluIlePhe
            1230              1250              1270
ggcactcaaggcaaaccagccatcgcccatcgtgacctcaagagccgcaacgtgctggtc
GlyThrGlnGlyLysProAlaIleAlaHisArgAspLeuLysSerArgAsnValLeuVal
            1290              1310              1330
aagagcaacttgcagtgttgcattgcagacctgggattggctgtgatgcactcgcaaagc
LysSerAsnLeuGlnCysCysIleAlaAspLeuGlyLeuAlaValMetHisSerGlnSer
            1350              1370              1390
agcgattacctggacattggtaacaaccccgagtgggtaccaagagatacatggcaccc
SerAspTyrLeuAspIleGlyAsnAsnProArgValGlyThrLysArgTyrMetAlaPro
            1410              1430              1450
gaggtgctggatgagcagatccgcacagactgttttgagtcgtacaagtggacagacatc
GluValLeuAspGluGlnIleArgThrAspCysPheGluSerTyrLysTrpThrAspIle
            1470              1490              1510
tgggccttcggcttagtgctatgggagattgcccggcggaccatcatcaatggcattgtg
TrpAlaPheGlyLeuValLeuTrpGluIleAlaArgArgThrIleIleAsnGlyIleVal
            1530              1550              1570
gaggactacaggccaccttctatgacatggtacccaatgacccagttttgaggacatg
GluAspTyrArgProProPheTyrAspMetValProAsnAspProSerPheGluAspMet
            1590              1610              1630
aaaaaggtggtgtgtgttgaccagcagaccccaccatccctaaccgactggcagcagat
LysLysValValCysValAspGlnGlnThrProThrIleProAsnArgLeuAlaAlaAsp
            1650              1670              1690
ccggtcctctccgggctggcccagatgatgcgagagtgctggtaccccaacccctccgct
ProValLeuSerGlyLeuAlaGlnMetMetArgGluCysTrpTyrProAsnProSerAla
            1710              1730              1750
cgcctcaccgcactgcgcataaagaagacattacagaagctcagccagaatccagagaaa
ArgLeuThrAlaLeuArgIleLysLysThrLeuGlnLysLeuSerGlnAsnProGluLys
            1770
cccaaagtgattcactag
ProLysValIleHisEnd
```

FIG. 3b

```
                    60                      80                    10
atggaggcggcgtcggctgctttgcgtcgctgcctgcttctcatcgtgttggtggcggcg
MetGluAlaAlaSerAlaAlaLeuArgArgCysLeuLeuLeuIleValLeuValAlaAla
0                   120                     140                   16
gcgacgctgctcccgggggcgaaggcattacagtgtttctgccacctctgtacaaaggac
AlaThrLeuLeuProGlyAlaLysAlaLeuGlnCysPheCysHisLeuCysThrLysAsp
0                   180                     200                   22
aattttacttgtgagacagatggtctctgctttgtctcagtcaccgagaccacagacaaa
AsnPheThrCysGluThrAspGlyLeuCysPheValSerValThrGluThrThrAspLys
0                   240                     260                   28
gttatacacaatagcatgtgtatagctgaaatcgacctaattccccgagacaggccattt
ValIleHisAsnSerMetCysIleAlaGluIleAspLeuIleProArgAspArgProPhe
0                   300                     320                   34
gtttgtgcaccatcttcaaaaacaggggcagttacgtattgctgcaatcaggatcactgc
ValCysAlaProSerSerLysThrGlyAlaValThrTyrCysCysAsnGlnAspHisCys
0                   360                     380                   40
aataaaatagaactcccaactacaggaccttttcagaaaagcagtcagctggcctcggt
AsnLysIleGluLeuProThrThrGlyProPheSerGluLysGlnSerAlaGlyLeuGly
0                   420                     440                   46
cctgtggagctggcagctgtcattgctggtccagtctgcttcgtctgcattgcacttatg
ProValGluLeuAlaAlaValIleAlaGlyProValCysPheValCysIleAlaLeuMet
0                   480                     500                   52
ctgatggtctatatctgccataaccgcactgtcattcaccaccgcgtgccaaatgaagag
LeuMetValTyrIleCysHisAsnArgThrValIleHisHisArgValProAsnGluGlu
0                   540                     560                   58
gatccctcactagatcgcccttcatttcagagggcaccaccttaaaagatttaatttat
AspProSerLeuAspArgProPheIleSerGluGlyThrThrLeuLysAspLeuIleTyr
0                   600                     620                   64
gatatgacaacatcagggtctggatcaggtttaccactgcttgttcaaagaacaattgca
AspMetThrThrSerGlySerGlySerGlyLeuProLeuLeuValGlnArgThrIleAla
0                   660                     680                   70
aggaccattgtgctacaagaaagcatcggcaaaggtcggtttggagaagtttggcgaggc
ArgThrIleValLeuGlnGluSerIleGlyLysGlyArgPheGlyGluValTrpArgGly
0                   720                     740                   76
aaatggcggggagaagaagttgccgtgaagataTTCTCTTCTAGAGAAGAACGTTCATGG
LysTrpArgGlyGluGluValAlaValLysIlePheSerSerArgGluGluArgSerTrp
0                   780                     800                   82
TTCCGAGAGGCAGAGATTTATCAGACTGTAATGTTACGCCATGAAAATATCCTGGGGTTT
PheArgGluAlaGluIleTyrGlnThrValMetLeuArgHisGluAsnIleLeuGlyPhe
0                   840                     860                   88
ATAGCAGCAGACAACAAAGACAATGGTACATGgactcagctgtggttggtgtcggattat
IleAlaAlaAspAsnLysAspAsnGlyThrTrpThrGlnLeuTrpLeuValSerAspTyr
0                   900                     920                   94
catgagcatggatccctttcgattacttgaatagatacactgttactgtggaaggaatg
HisGluHisGlySerLeuPheAspTyrLeuAsnArgTyrThrValThrValGluGlyMet
```

FIG. 4a

```
0              960              980              100
atcaaactcgctctgtccacggcaagtggtcttgcccatcttcacatggagattgttggt
IleLysLeuAlaLeuSerThrAlaSerGlyLeuAlaHisLeuHisMetGluIleValGly
0             1020             1040             106
acccaaggaaaaccagctattgccCATAGAGATTTGAAATCAAAGAATATCTTGGTGAAG
ThrGlnGlyLysProAlaIleAlaHisArgAspLeuLysSerLysAsnIleLeuValLys
0             1080             1100             112
AAAAATGGAACCTGTTGTATTGCAGATTTGGGACTTGCTGTGAGACATGATTCTGCCACA
LysAsnGlyThrCysCysIleAlaAspLeuGlyLeuAlaValArgHisAspSerAlaThr
0             1140             1160             118
GATACAATTGATATTGCTCCAAACCACAGAGTAGGCACTAAAAGGtatatggcccctgaa
AspThrIleAspIleAlaProAsnHisArgValGlyThrLysArgTyrMetAlaProGlu
0             1200             1220             124
gttctagatgattccataaatatgaaacattttgaatccttcaaacgtgctgacatctat
ValLeuAspAspSerIleAsnMetLysHisPheGluSerPheLysArgAlaAspIleTyr
0             1260             1280             130
gcaatgggcttagtattctgggaaatcgctcgacgctgttccattggcggaatccacgaa
AlaMetGlyLeuValPheTrpGluIleAlaArgArgCysSerIleGlyGlyIleHisGlu
0             1320             1340             136
gactaccagttgccttactatgatcttgtaccttctgatccatccgttgaagaaatgaga
AspTyrGlnLeuProTyrTyrAspLeuValProSerAspProSerValGluGluMetArg
0             1380             1400             142
aaagtagtttgtgaacagaagttaaggccaaatattcccaacagatggcagagctgtgag
LysValValCysGluGlnLysLeuArgProAsnIleProAsnArgTrpGlnSerCysGlu
0             1440             1460             148
gccttgagagtgatggccaaaattatgagagaatgttggtatgccaatggagcagctagg
AlaLeuArgValMetAlaLysIleMetArgGluCysTrpTyrAlaAsnGlyAlaAlaArg
0             1500             1520             154
ctgacagctttgcgaattaaaaaaacattgtcacagctcagccaacaggaaggcatcaaa
LeuThrAlaLeuArgIleLysLysThrLeuSerGlnLeuSerGlnGlnGluGlyIleLys
0
atgtaa
MetEnd
```

FIG. 4b

FIG. 5a MISr1 (BCORI insert size ~2.7 kb, specific oligo sequence: 5'-GTCTACCAGAAGGGCTGCTT-3') (SEQ ID NO: 5) All inserts are in the ECORI site of plasmid pBluescript I SK(-).

FIG. 5b MISr2a (~1.4 kb, 5'-CCGGAGCCTCCTCCTTCTTC-3') (SEQ ID NO: 6)

FIG. 5c MISr2b (~2.1 kb, 5'-TCCCTACTGGGTTTGAGACA-3') (SEQ ID NO: 7)

FIG. 5d MISr3 (~3.2 kb, 5'-GCTGCGGGAGCCTGAACCAG-3') (SEQ ID NO: 8)

FIG. 5e MISr4 (~2.8 kb, 5'-AAATCCAATGTTTGAATACT-3') (SEQ ID NO: 9)

DNA ENCODING A RECEPTOR FOR MÜLLERIAN INHIBITORY SUBSTANCE, MISR1, AND CORRESPONDING VECTORS, CELLS, PROBES, AND RECOMBINANT METHODS

The work described herein was supported in part by grant No. Ca17393 from the National Institutes of Health. The U.S. government has certain rights in the invention.

This is a continuation of application Ser. No. 08/029,673, filed Mar. 11, 1993, now abandoned, which is a continuation-in-part of U.S. Ser. No. 07/853,396, filed Mar. 18, 1992, now abandoned.

BACKGROUND OF THE INVENTION

The field of the invention is mammalian receptor proteins, and nucleic acids encoding same.

Müllerian Inhibiting Substance (MIS) plays a critical role in normal sexual dimorphism as one of the early manifestations of the SRY genetic switch (Gubbay et al., Nature 346:245–250, 1990; Sinclear et al., Nature 346:240–244, 1990; Berta et al., Nature 348:448–350, 1990; Haqq et al., Proc. Natl. Acad. Sci. USA 90:1097–1101, 1993). MIS subsequently causes regression of the Müllerian duct, inhibition of aromatase activity which leads to increased synthesis of testosterone, and probably morphological differentiation of the sex cords as seminiferous tubules, thus assuring the male phenotype. Jost's seminal observations in the late 1940s first defined a "Müllerian Inhibitor" responsible for regression of the Müllerian ducts in the male mammalian embryo (Jost, Arch. Anat. Micro. Morphol. Exp. 36:271–315, 1947). MIS was found to be a 140 kDa protein produced by the Sertoli cell (Blanchard and Josso, Pediatr. Res. 8:968–971, 1974); it was subsequently purified to homogeneity (Budzik et al., Cell 21:909–915, 1980, Cell 34:307–314, 1983; Picard et al., Mol. Cell. Endocrinol. 34:23, 1984), using the bioassay of Müllerian duct regression devised by Picon (Arch. Anat. Microsc. Morphol. Exp. 58:1–19, 1969) as a monitor. The bovine and human genes were cloned (Cate et al., Cell 45:685–698, 1986a) and subsequently expressed and produced in mammalian cell cultures (Cate et al., Cold Spring Harbor Symposium 51:641–647, 1986b; Epstein et al., In Vitro Cellular and Developmental Biol. 25:213–216, 1989); more recently, the rat (Haqq et al., Genomics 12:665–9, 1992) and mouse (Munsterberg and Lovell-Badge, Development 13:613–624, 1991) genes have also been cloned. Overexpression of MIS in transgenic female mice caused regression of Müllerian ducts and seminiferous tubular differentiation (Behringer et al., Nature 345:167–70, 1991). Several patients with Retained Müllerian Duct Syndrome were found to have point mutations in the MIS gene (Knebelman et al., Proc. Natl. Acad. Sci. 88:3767–3771, 1991), which has been localized to the short arm of chromosome 19 (Cohen-Hagenaur et al., Cytogenet. Cell. Genet. 44:2–6, 1987). In mice, the MIS gene is located on chromosome 10 (King et al., Genomics 11:273–283, 1991).

MIS is a member of the large TGF-β family, which includes, besides TGF-β (Derynck et al., Nature 316:701–5, 1985), activin (Ling et al., Nature 321:779–82, 1986; Vale et al., Nature 321:776–779, 1986); inhibin (Mason et al., Nature 318:659–63, 1985); decapentaplegia complex (Padgett et al., Nature 325:81–4, 1987); Vg–1 (Weeks and Melton, Cell 51:861–7, 1987); and bone morphogenesis factors (Wozney et al., Science 242:1528–34, 1988). A common feature of some members of this gene family is that latent precursor can be activated by plasmin cleavage and release of 25 kDa carboxyl terminal dimers.

Although originally defined and named by its ability to cause regression of the Müllerian duct, other functions have emerged for MIS. Its localization to the preantral and smaller antral follicles by immunocytochemical techniques (Takahashi et al., Biol. Reprod. 35:447–53, 1986a; Bezard et al., J. Reprod. Fertil. 80-509-16, 1987; Ueno et al., Endocrinol. 125:1060–1066, 1989a; Ueno et al., Endocrinology 124:1000–1006, 1989b) and its ability to inhibit germinal vesicle breakdown (Takahashi et al., Mol-Cell-Endocrinol. 47:225–34, 1986b; Ueno et al., Endocrinology 123:1652–1659, 1988) led to the hypothesis that it was involved in meiotic inhibition in the ovary. Developmental and experimental correlations support such a function in the testis (Taketo, et al., Devel. Biol. 146:386–395, 1991), where analysis of timing of expression suggests that MIS may be responsible for inhibition of germ cell division. Hutson and Donahoe (Endocrine Reviews 7:270–283, 1986) speculated that MIS may also play a role in the transabdominal portion of testicular descent, and Vigier et al. (Development 100:43–55, 1987; Proc. Natl. Acad. Sci. USA 86:3684–8, 1989) have provided evidence that it functions as an inhibitor of aromatase in developing ovaries. Catlin et al. (Am. J. of Obstet. and Gynecol. 159:1299–1303, 1988; Am. Rev. Resp. Dis. 141:466–470, 1990) showed that MIS decreases surfactant accumulation in fetal lungs, thus contributing to the male preponderance in newborn infants of Respiratory Distress Syndrome. The development of a specific serum MIS ELISA (Hudson et al., J. Clin. and Metab. 70:16–22, 1990; Josso et al., J. Clin. Endocrinol. Metab. 70:23-7, 1990) has led to its experimental use as a diagnostic tool for the elucidation of the pathophysiology of ambiguous genitalia in the newborn, and for the use of serum MIS as a marker of granulosa and sex cord tumors in the adult female. Furthermore, the extraordinarily high MIS level observed by Gustafson et al. (New Eng. J. Med. 326:466–71, 1992) in a patient with a sex cord tumor (3200 ng/ml, compared to a normal level of 2–3 ng/ml) provides evidence that MIS is not toxic at these levels.

The role of MIS as a fetal inhibitor has led to the hypothesis that it might act as a tumor inhibitor, particularly of tumors emanating from the Müllerian ducts (Donahoe et al., Science 205:913–915, 1979; Donahoe et al., Ann. Surg. 194:472–480, 1981; Fuller et al., J. Clin. Endocrin. Metab. 54:1051–1055, 1982; Fuller et al., Gynecol. Oncol. 17:124–132, 1984; Fuller et al., Gynecol. Oncol. 22:135–148, 1985). Experimental evidence has accumulated supporting the ability of recombinant human MIS to exert an antiproliferative effect against genital tract tumors in colony inhibition assays, subrenal capsule assays (Chin, et al., Cancer Research, 51:2101–6, 1991), and now metastases assays, and more recent evidence has shown an antiproliferative effect against a series of human ocular melanomas (Parry et al., Cancer Research 51:1182–6, 1992). MIS has been shown to block tyrosine autophosphorylation of EGF receptors (Coughlin et al., Mol. and Cell. Endocrin. 49:75–86, 1987; Cigarroa et al., Growth Factors 1:179–191, 1989).

Inhibin, another member of the TGF-beta family described above, is primarily secreted by Sertoli and granulosa cells of the male and female gonad. This nonsteroidal regulatory hormone, first described in 1932 (McCullagh, Science 76:19–20), acts specifically to inhibit FSH release from the pituitary (Vale et al., Recent Prog. Horm. Res. 44:1–34, 1988). Biologically active inhibin, however, was not purified and characterized well until the successful cloning of its genes in 1985–86 (Mason et al., Nature 318:659, 1985; Forage et al., Proc. Natl. Acad. Sci. USA 83:3091, 1986; Mayo et al., Proc. Natl. Acad. Sci. USA 83:5849, 1986; Esch et al., Mol. Endocrinol. 1:388, 1987). Inhibin was shown at that time to be a glycoprotein heterodimer composed of an alpha-chain and one of two distinct beta-chains (beta-A, beta-B) (Mason et al., Blochem. Biophys. Res. Comun. 135:957, 1986). The alpha chain is processed from an initial species of 57 kDa to form an 18 kDa carboxyl-terminal peptide, while the mature beta chain of 14 kDa is cleaved from the carboxyl-terminus of a 62 kDa precursor, which would then account for the biologically active 32 kDa species which predominates in serum (DeKretser and Robertson, Biol. Reprod. 40:3347, 1989). Many other forms of bioactive inhibin with MW's of 32–120 kDa, however, have been isolated as well (Miyamoto et al., Biochem. Biophys. Res. Commun. 136:1103–9, 1986). In addition, beta-chain dimers (beta-A/beta-A or beta-A/beta-B) which selectively stimulate FSH secretion from the pituitary have been identified and are called activin A and activin AB, respectively (Vale et al., Nature 321:776, 1986; Ling et al., Nature 321:779, 1986).

As is the case with MIS, many additional functions have been postulated for inhibin and its subunits besides FSH regulation. Inhibin alpha, beta-A, and beta-B subunit RNAs have been shown to be expressed in a variety of rat tissues, including the testis, ovary, placenta, pituitary, adrenal gland, bone marrow, kidney, spinal cord, and brain (Meunier et al., Proc. Natl. Acad. Sci. USA 85:247–51, 1988). The pattern of testicular inhibin secretion appears to be developmentally regulated. In the rat, inhibin increases during maturation until 30–40 days after birth, after which values rapidly return to juvenile levels (Au et al., Biol. Reprod. 35:37, 1986). Inhibin subunits also seem to have a paracrine effect on Leydig and theca interna cell androgen synthesis (Hsueh et al., Proc. Natl. acad. Sci. USA 84:5082–6, 1987). Many studies have demonstrated the changes in inhibin which occur throughout the estrus cycle, and therefore, its role in modulating FSH in adult females (Hasegawa et al., J. Endocrinology 121:91–100, 1989; McLachlan et al., J. Clin. Endo. Metab. 65:954–61, 1987). Furthermore, changes in local inhibin concentrations may be involved in the regulation of ovarian folliculogenesis (Woodruff et al., Science 239:1296–9, 1988; Woodruff et al., Endocrinology 127:3196–205, 1990). Bioactive inhibin has been shown to be produced by human placental cells in culture and to be involved in a short-loop feedback between gonadotropin-releasing hormone and human chorionic gonadotropin (Petraglia et al., Science 237:187–9, 1987). Finally, a number of patients with ovarian granulosa cell tumors have been described who had markedly elevated serum inhibin levels secondary to tumor production of this hormone (Lappohn et al., NEJM 321:790–3, 1989).

Most of the data that exist concerning serum inhibin levels in humans have been obtained using a heterologous radioimmunoassay comprised of a polyclonal antibody to purified, intact bovine inhibin and radiolabeled 32 kDa bovine inhibin (McLachlan et al., Mol. Cell. Endocrinol. 46:175–85, 1986). Such studies have evaluated normal cycling females and adult males (McLachlan et al., J. Clin. Endo. Metab. 65:954–61, 1987; McLachlan et al., J. Clin. Invest. 82:880–4, 1988), pubertal males (Burger et al., J. Clin. Endo. Metab. 67:689–694, 1988), normal pregnant women (Abe et al., J. Clin. Endocrinol. Metab. 71:133–7, 1990), and a variety of reproductive disorders (Scheckter et al., J. Clin. Endocrinol. Metab. 67:1221–4, 1988; DeKretser et al., J. Endocrinol. 120:517–23, 1989). However, recent work has shown that this assay detects inhibin alpha-subunits as well as intact dimeric hormone, and, therefore, these results should be interpreted with caution (Schneyer et al., J. Clin. Endocrinol. Metab. 70:1208–12, 1990).

SUMMARY OF THE INVENTION

The invention features novel isolated DNAs of the TGF-β receptor family, which isolated DNAs encode, for example, MIS receptors, inhibin receptors, and bone morphogenesis protein (BMP) receptors; these receptors are, e.g., those of a mammal such as a rat, mouse, rabbit, guinea pig, hamster, cow, pig, horse, goat, sheep, or human. The invention also includes vectors (e.g., plasmids, phage, or viral nucleic acid) or cells (prokaryotic or eukaryotic) which contain such DNAs, and the polypeptides produced by expression of such DNAs (for example, by a cell transformed with and capable of expressing a polypeptide from the DNA). By "isolated DNA" is meant a DNA that is not immediately contiguous with both of the coding sequences with which it is immediately contiguous (i.e., one at the 5' and one at the 3' end) in the naturally-occurring genome of the organism from which the DNA of the invention is derived. The term thus encompasses, for example, a cDNA or a genomic DNA fragment produced by PCR or restriction endonuclease treatment, whether such cDNA or genomic DNA fragment is incorporated into a vector, integrated into the genome of the same or a different species than the organism from which it was originally derived, linked to an additional coding sequence to form a hybrid gene encoding a chimeric polypeptide, or independent of any other DNA sequences. The DNA may be double-stranded or single-stranded, sense or antisense. Examples of isolated DNAs of the invention include those which encode amino acid sequences substantially the same as those shown in FIG. 1 (SEQ ID NO: 14), FIG. 2 (SEQ ID NO: 15), FIG. 3 (SEQ ID NO: 16), and FIG. 4 (SEQ ID NO: 16); and those having sequences which hybridize under conditions of high or moderate stringency to the coding sequence of one of the plasmids included in the ATCC deposit designated No. 75213: misrl, misr2A, misr2B, misr3, or misr4. High stringency conditions are herein defined as the following: hybridizing with 50% deionized formamide, 800 mM NaCl; 20 mM Pipes, pH 6.5, 0.5% SDS, 100 µg/ml denatured, sonicated salmon sperm DNA at 42° C. for 12–20 hours, washing with 30 mM NaCl/3.0 mM sodium citrate (0.2× SSC)/0 1% SDS at 55° C., while moderate stringency conditions are as follows: hybridizing with 50% deionized formamide, 800 mM NaCl; 20 mM Pipes, pH 6.5, 0.5% SDS, 100 µg/ml denatured, sonicated salmon sperm DNA at 42° C. for 12–20 hours, washing with 75 mM NaCl/7.5 mM sodium citrate (0.5× SSC)/0.1% SDS at 55° C.

The isolated DNA of the invention may be under the transcriptional control of a heterologous promoter (i.e., a promoter other than one naturally associated with the given receptor gene of the invention), which promoter for example, may direct the expression of the DNA of the invention in a particular tissue or at a particular stage of development.

Also within the invention is a substantially pure preparation of an MIS receptor or inhibin receptor protein, or another of the receptor proteins of the invention, prepared, for example, from a natural source, from an expression system expressing the isolated DNA of the invention, or by synthetic means. This protein may, for example, have a sequence the same as, or substantially identical to, that shown in FIG. 1 (SEQ ID NO: 14), FIG. 2 (SEQ ID NO: 15), FIG. 3 (SEQ ID NO: 16), or FIG. 4 (SEQ ID NO: 17), or that encoded by any one of the plasmids deposited as ATCC Accession No. 75213. By "substantially pure preparation" is meant that the preparation is at least 70% free of those proteins with which the protein of the invention is naturally associated in the tissue(s) in which it naturally occurs. In preferred embodiments, the preparation is at least 90% free of such contaminating proteins.

Also within the invention is a substantially pure nucleic acid at least 20 nucleotides in length (preferably at least 50 nucleotides, more preferably at least 100 nucleotides, and most preferably 1000 nucleotides or more in length) which hybridizes under highly stringent conditions to the coding region of a plasmid included in the ATCC deposit designated No. 75213. By "substantially pure nucleic acid" is meant an RNA or DNA molecule which is substantially free of those other nucleic acid molecules, if any, with which it is naturally associated in the cell from which it was originally derived (i.e., such other nucleic acid molecules make up less than 50% of the total number of nucleic acid molecules in the preparation). By "other nucleic acid molecules" is meant nucleic acid molecules which do not encode the same polypeptide as the nucleic acid of the invention. In preferred embodiments, less than 20%, and more preferably less than 10% of the preparation consists of such other nucleic acid molecules. Such a nucleic acid may be employed in a Northern analysis or in situ hybridization assay for determining the level of expression of the gene in a biological sample, which assay would include the steps of (1) providing the isolated DNA of the invention, which isolated DNA includes single stranded antisense DNA; (2) contacting, under hybridizing conditions (preferably of high stringency), the isolated DNA with a biological sample suspected of containing mRNA encoding a receptor of the invention; and (3) determining the level and/or pattern of hybridization of the isolated DNA in the biological sample, the level or pattern of hybridization in the sample being indicative of the level or pattern of expression of the gene encoding the receptor.

As described below, the receptor proteins of the invention (or a ligand-binding portion of such receptors) can be used for a number of purposes. They can be fixed by standard means to a matrix material to form an affinity matrix capable of binding ligand, useful for purifying ligand, for screening for inhibitors of the ligand/receptor interaction, or for determining the amount of ligand present in a given biological sample. They can be used in an assay including the steps of (1) providing the polypeptide of the invention; (2) contacting the polypeptide with a biological sample suspected of containing MIS, inhibin, or a biologically active fragment thereof; and (3) determining the amount of receptor/ligand complex formation in the sample, such amount of complex formation being indicative of the amount of MIS or inhibin activity in the sample. They can also be used to generate monoclonal or polyclonal antibodies specific for (i.e., capable of forming an immune complex with) such receptors, which antibodies would be useful in a method for detecting the presence of an MIS or inhibin receptor in a biological sample such as serum or tumor cells. Such a method would include the steps of (1) contacting the antibody with a biological sample suspected of containing an MIS or inhibin receptor, and (2) detecting immune complex formation between the antibody and a component of the biological sample, wherein such immune complex formation is indicative of the presence of such a receptor in the sample. Furthermore, such antibodies can be linked to a cytotoxic agent, thereby forming an immunotoxin useful for targeting and killing or disabling cells bearing the receptor of the invention.

Other features and advantages of the invention will be apparent from the following detailed description, and from the claims.

DETAILED DESCRIPTION

The drawings are first described.
Drawings FIG. 1 is a representation of the DNA coding sequence of misrl (SEQ ID NO: 1), and the corresponding amino acid sequence of the encoded receptor protein (SEQ ID NO: 14).

FIG. 2 is a representation of the DNA coding sequence (SEQ ID NO: 2) of two overlapping cloned cDNAs, misr2A and misr2B, and the corresponding amino acid sequence of the encoded receptor protein (SEQ ID NO: 15).

FIG. 3 is a representation of the DNA coding sequence of misr3 (SEQ ID NO: 3), and the corresponding amino acid sequence of the encoded receptor protein (SEQ ID NO: 16).

FIG. 4 is a representation of the DNA coding sequence of misr4 (SEQ ID NO: 4), and the corresponding amino acid sequence of the encoded receptor protein (SEQ ID NO: 17).

FIG. 5A is a partial, 20-nucleotide sequence of misrl (SEQ ID NO: 5).

FIG. 5B is a partial, 20-nucleotide sequence of misr2A (SEQ ID NO: 6).

FIG. 5C is a partial, 20-nucleotide sequence of misr2B (SEQ ID NO: 7).

FIG. 5D is a partial, 20-nucleotide sequence of misr3 (SEQ ID NO: 8).

FIG. 5E is a partial, 20-nucleotide sequence of misr4 (SEQ ID NO: 9).

Figure 6A:
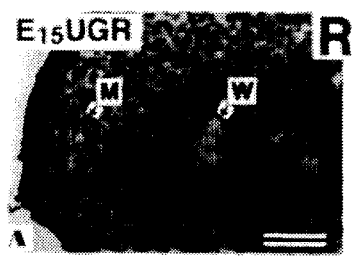
Figure 6B:
Figure 6C:
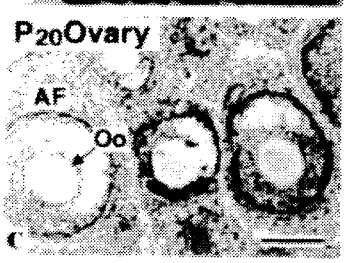
Figure 6D:
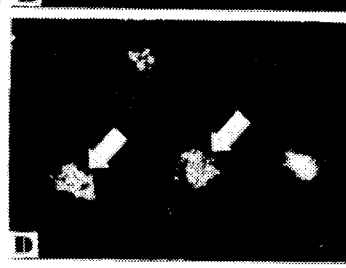
Figure 6E:
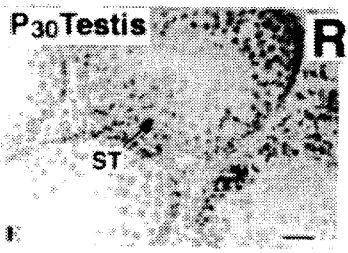
Figure 6F:
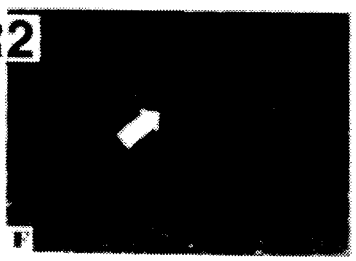

FIGS. 6A–6F are photographs showing in situ hybridization of the urogenital ridge (UGR), ovary, and testis with a riboprobe (R1) derived from misrl (SEQ ID NO: 1) and a second riboprobe (R2) derived from misr2 (SEQ ID NO: 2). FIGS. 6A, 6C and 6E are representative brightfield views in which hybridization signals appear as black granules (Bar= 100 μm); FIGS. 6B, 6D, and 6F are identical darkfield views in which RNA message appears as bright spots (heavy arrows). In FIGS. 6A and 6B, R1 hybridization signal in the 15-day (E15) fetal male UGR is conspicuous over the mesenchyme of the Mullerian duct (M), but not over the adjacent Wolffian duct (W). In FIGS. 6C and 6D, R1 signal is also intense over the oocytes (Oo) of preantral and antral follicles (AF) of the postnatal day 20 (P20) ovary, with less intense signal over their adjacent granulosa cells. Two separate R1 riboprobes were used to confirm these findings in FIGS. 6A–6D: one from the 5' extracellular domain and one from the 3' intracellular region of the coding sequence. In FIGS. 6E and 6F, R2 signal localizes in a heterogeneous pattern to seminiferous tubules (ST) of the postnatal day 30 (P30) testis. No R2 message was detected in the fetal Mullerian duct or the pubertal and adult ovary. Both R1 and R2 signals were found in the female postnatal anterior pituitary and hippocampus (data not shown).

FIGS. A7 and 7B shows the results of Northern analysis of fetal and postnatal rat tissues for MISR1-MISR4 mRNA expression. The blot shown in FIG. 7A was hybridized sequentially with misr1, misr3 and pyruvate kinase (pk) probes, while the blot shown in FIG. 7B was probed serially with misr2a/misr2b, misr4 and pk. Approximately 4.0 kb MISR1, 4.4 and 1.5 kb MISR2, 4.4 kb MISR3, and 6 kb MISR4 transcripts were all detected in the 15-day (E15) fetal urogenital ridge (UGRidge) and postnatal day 1 (P1) testis and ovary. Surprisingly, mRNAs for MISR1, MISR2, and MISR4 were abundant in the 21-day (E21) fetal brain. MISR1-MISR4 message was also present in the E21 fetal lung; other E21 issues, such as the lung, heart, and stomach, contained variable levels of MISR1 and MISR2 mRNA.

Figure 8:
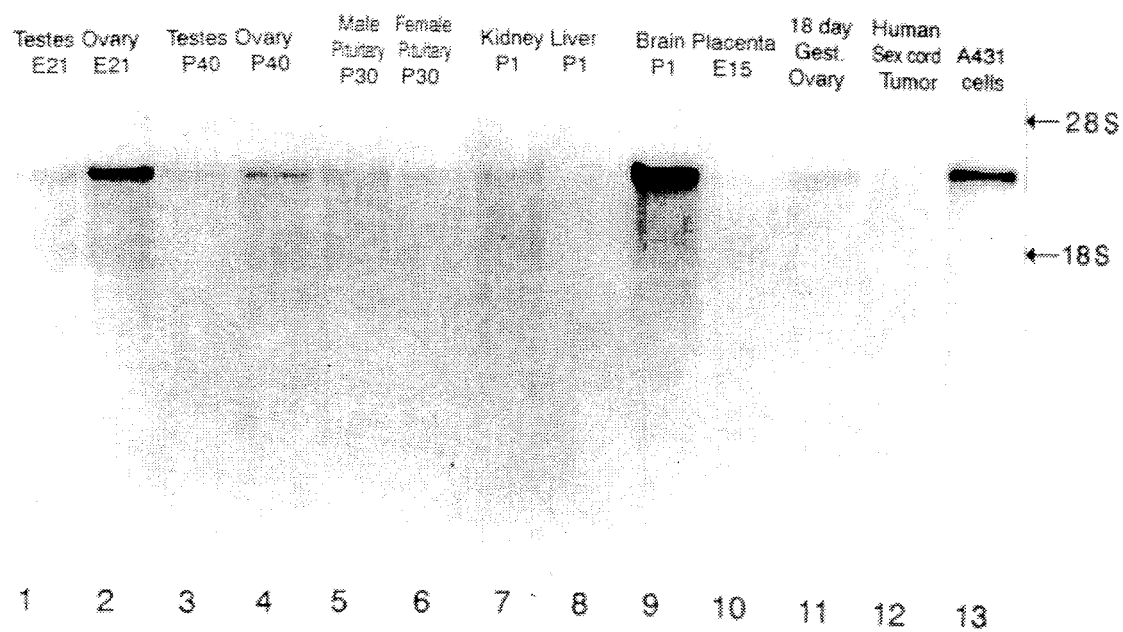

FIG. 8 illustrates the results of Northern analysis of a variety of tissues/cells with an misrl (MIS receptor; SEQ ID NO: 1) cDNA probe. A specific hybridization signal is seen with RNA extracted from rat testicular, ovarian, brain, and pituitary tissues. Lane 1, 21-day fetal rat testes; 2, 21-day fetal rat ovaries; 3, postnatal day 40 rat testis; 4, postnatal day 40 rat ovary; 5, postnatal day 30 male rat pituitary; 6, postnatal day 30 female rat pituitary; 7, postnatal day 1 male rat kidney; 8, postnatal day 1 male rat liver; 9, postnatal day 1 male rat brain; 10, placenta from 15-days gestation; 11, adult ovary from 18 days gestation; 12, human sex cord tumor fragment; 13, A431 human vulvular squamous carcinoma cell line. (10 µg of total RNA per lane, except 2 µg of poly A+ RNA in lane 13; 8 day exposure.)

Figure 9:
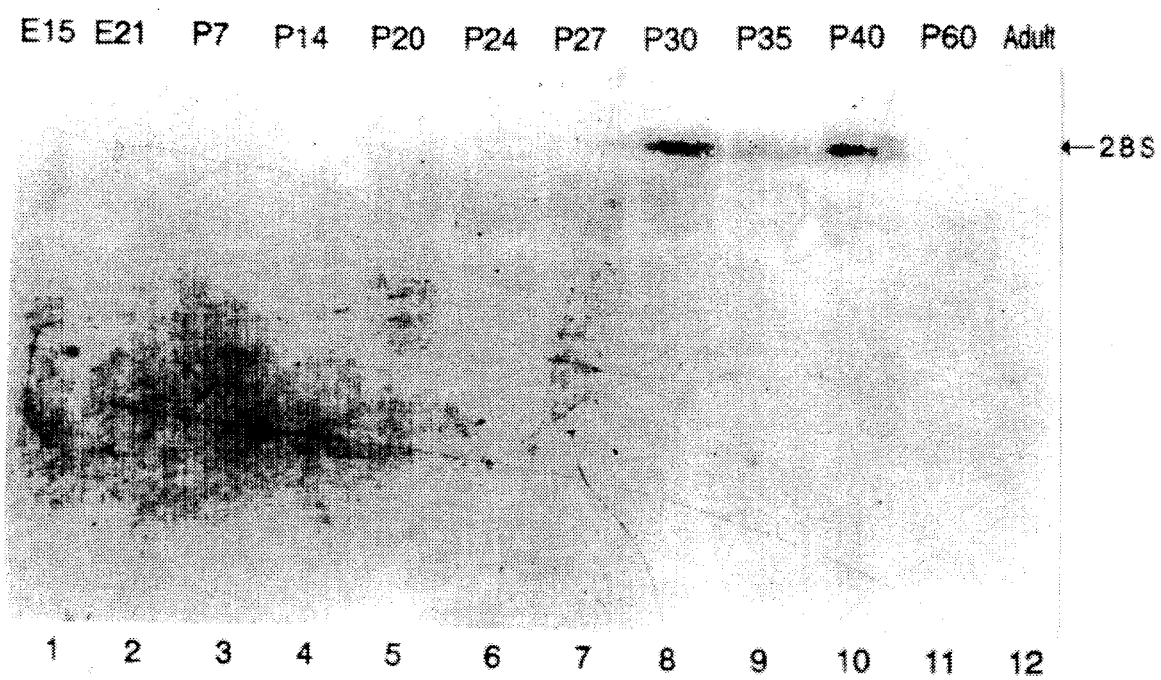

FIG. 9 illustrates the results of Northern analysis of fetal, prepubertal, pubertal, and adult rat testicular tissue with an misr2 (inhibin receptor; SEQ ID NO: 2) cDNA probe. Maximal hybridization signal was detected with postnatal day 35 and 40 testicular RNA, with a rapid decrease in detectable message by 60 days. This pattern of RNA expression exactly mirrors the known ontogeny of inhibin expression in the maturing rat. Hybridization signal was also detected with rat ovarian and brain tissue (not shown). E15 and E21 samples are from tests collected at days 15 and 21 of gestation, respectively; P7, P14, P20, P24, P27, P30, P35, P40, and P60 samples are all from postnatal animals. (10 µg of total RNA per lane; 4 day exposure.)

PREPARATION OF THE ISOLATED DNAS OF THE INVENTION

Four different isolated DNAs of the invention were prepared by cloning from a rat embryonic urogenital ridge cDNA library, as described below. Some alternative means of preparing the isolated DNAs of the invention, using the information provided herein and standard techniques, are as follows:

(1) A nucleic acid having the nucleotide sequence shown in any one of FIGS. 1–4 (SEQ ID NOs: 1–4, respectively), or a nucleic acid encoding the amino acid sequence shown in that figure but, owing to the degeneracy of the genetic code, having a nucleotide sequence different from that shown in the figure, may be synthesized by standard chemical means as generally applied to synthesis of oligonucleotides.

(2) A nucleic acid hybridization probe containing at least 20 nucleotides, and preferably at least 50 nucleotides, of one of the DNA sequences shown in any of FIGS. 1–4 (SEQ ID NOs: 1–4) may be prepared by standard methodology and used to probe a "library" of the five plasmids making up the ATCC deposit designated No. 75213. For example, a probe which includes at least a portion of the nucleotide sequence shown in FIG. 1 (SEQ ID NO: 1), such as the partial sequence shown in FIG. 5A (SEQ ID NO: 5), will hybridize under high stringency conditions (e.g., hybridizing in 50% deionized formamide, 800 mM NaCl, 20 mM Pipes, pH 6.5, 0.4% SDS, 500 µg/ml denatured, sonicated salmon sperm DNA at 42° C. for 12-20 hours; and washing in 30 mM NaCl, 3.0 mM sodium citrate, 0.5% SDS at 65° C.) solely with a plasmid containing the complementary sequence, and so would identify clones containing the misrl sequence. Similarly, the partial sequences shown in FIGS. 5B, 5C, 5D, and 5E (SEQ ID NOs: 6–9, respectively) can be used to identify misr2A, misr2B, misr3, and misr4, respectively. The desired plasmid can be selected as follows:

The plasmid samples deposited with the ATCC and given accession No. 75123 contain 500 ng of each of the five plasmid DNAs in 50 µl final volume. A given clone may be isolated from such a sample by transforming 1 µl of DNA from the sample into bacteria HB 101 by either chemical transformation or electroporation. The transformed bacteria are selected on 1.5% agar plates containing 50 µg/ml ampicillin. Ampicillin-resistant colonies are picked individually and grown in 5 ml of LB broth containing 50 µg/ml ampicillin. The plasmid DNA of a few colonies may then be isolated using the standard plasmid DNA mini-prep procedure. The mini-prep DNA is then characterized by means of a DNA dot-blot, using as hybridization probe one of the $^{32}$P-labelled misr1, misr2A, misr2B, misr3, or misr4-specific probes discussed above. Alternatively, a cDNA library prepared from a tissue that expresses the gene of interest (such as the rat urogenital ridge cDNA library described below), or a genomic library from rat, can be probed with such a hybridization probe under highly stringent conditions.

(3) An isolated DNA prepared by any of the methods outlined herein (including the methods originally used to obtain the DNAs of the invention) may be used to probe an appropriate cDNA library or genomic DNA library from any vertebrate species. The stringency of the hybridization conditions would be adjusted as necessary to obtain the desired homolog, while minimizing the number of related but distinct receptor (such as TGF-B or activin receptor) sequences picked up in the assay. It is expected that hybridization and wash conditions such as the highly stringent conditions set forth in (2) above would be adequate; if necessary, the stringency may be increased or decreased, without undue experimentation, using methods well known to those of ordinary skill in the art (see, e.g., Sambrook et al., Molecular Cloning: A Laboratory Manual, Cold Spring Harbor Laboratory, Cold Spring Harbor, N.Y., 1989). A given cloned cDNA or genomic DNA would be identified as a homolog of misr1, misr2, misr3, or misr4 by means of sequence comparison, wherein an encoded amino acid sequence that is at least 70% identical to the amino acid sequence encoded by any one of misrl (SEQ ID NO: 1), misr2 (SEQ ID NO: 2), misr3 (SEQ ID NO: 3), or misr4 (SEQ ID NO: 4) is considered to be a homolog of that receptor. Given the apparently ubiquitous occurrence of MIS, inhibin, and bone morphogenesis proteins (BMPs) among vertebrate species in which they have been sought, it is expected that most or all vertebrate species, and certainly all mammalian species, will be found to have genes encoding at least one MIS receptor, inhibin receptor, and BMP receptor which can be identified by the methods described herein. It is further expected, based upon the information disclosed herein, that many if not all such species will be found to harbor a plurality of isoforms of such receptor genes.

Each such homolog can be definitively identified as an MIS receptor, inhibin receptor, or BMP receptor by any of the following assays:

(a) Following transient transfection and expression of the putative receptor DNA in an appropriate expression system (i.e., a eukaryotic cell line, such as COS cells, that does not normally express the receptor), the cells are exposed to the suspected ligand (e.g., MIS, inhibin, or one of the BMPs [either recombinant or naturally occurring]) from the same species as the subject homolog receptor. The ligand can be labelled in order to allow detection of binding to the transfected cells (which presumably bear the recombinant receptor on their surfaces), or alternatively a labelled antibody specific for the ligand can be used to indicate whether or not the cells have bound ligand. Binding of the ligand (with or without crosslinking to the receptor) by transfected but not untransfected cells is evidence that the putative receptor DNA does encode a receptor specific for the ligand. Such experiments could be carried out using recombinant human MIS produced as disclosed in Cate et al., U.S. Pat. No. 5,047,336 (herein incorporated by reference), and purified by means of an affinity column using an anti-MIS monoclonal antibody, such as disclosed in Donahoe et al., U.S. Pat. No. 4,792,601 (herein incorporated by reference). The purified holo MIS is then proteolytically cleaved into an amino terminal fragment and a 24 kDa carboxyl terminal fragment, and the biologically active carboxyl terminal fragment is isolated and radiolabelled. Details of these procedures are provided in the Experimental Data section below. The biologically active form of inhibin (a 32 kDa inhibin carboxyl-terminal fragment) and the various BMPs may also be radiolabelled as described below. The specific binding and affinity constant can be calculated by using a molar excess of unlabelled ligand for competition.

(b) MIS, inhibin, or any of the BMPs can be fixed to an affinity matrix material by standard methods, and then used to assay for proteins which bind to the matrix: for example, the putative receptor protein expressed by cells transfected with a cloned DNA of the invention, and isolated from the cells' membranes by standard techniques, can be passed over a column of such affinity matrix material. In a variation on this technique, the putative receptor protein itself can be fixed to the matrix material, and a preparation including the ligand (MIS, inhibin, or a BMP) passed over the column.

(c) Eukaryotic cells which do not normally express an MIS, inhibin, or BMP receptor are transfected with the putative receptor DNA of the invention, and used, in accordance with standard procedures, to generate monoclonal antibodies which can differentiate between such transfected cells and identical but untransfected cells. These monoclonal antibodies are then labelled and used in immunohistochemical analysis of given tissues, in order to determine what tissues normally express the putative receptor DNA, and at what stages of development. A pattern of expression that correlates with the expected pattern (the expected pattern being determined, for example, by the pattern of binding of MIS, inhibin, or BMPs in such tissues) would provide evidence that the putative receptor DNA did indeed encode the predicted receptor.

(d) Monoclonal antibodies raised as described above could also be used in a competitive binding assay. A given tissue sample which, by virtue of its ability to bind natural or recombinant MIS, inhibin, or BMP, is known to bear naturally occurring MIS or inhibin receptors could be employed in a competitive binding assay with either labelled ligand and excess unlabelled antibody raised against the putative receptor (as described above), or labelled antibody and excess unlabelled ligand. Evidence that the ligand and the antibody compete for the same binding sites would support the conclusion that the putative receptor was indeed an MIS, inhibin, or BMP receptor.

(d) Another technique for confirming the identity of a putative receptor of the invention is by the use of Northern blots, probing the RNA of various tissues with a single-stranded hybridization probe made of labelled DNA encoding the putative receptor. The expression of putative receptor-specific genes in tissues known to be affected by MIS, inhibin, BMP, or another candidate ligand, including both normal and disease-state tissues, and the lack of detectible expression in other tissues known to be insensitive to the candidate ligand, is evidence that the putative receptor is indeed a receptor for the candidate ligand.

Use

The cDNAs of the invention, or fragments thereof long enough to serve as specific hybridization probes, can be duplicated by standard means by transfection into appropriate cells (e.g., bacterial cells), purified, and then used as hybridization probes in Northern or in situ hybridization analyses, in order to determine the level of expression of the relevant mRNA in a particular tissue sample. Alternatively, a vector encoding a receptor of the invention plus appropriate expression control elements can be transfected into a cell capable of expressing the receptor polypeptide. Such cells may express the polypeptide as a surface-anchored receptor, or may secrete the polypeptide or accumulate it within the cell. Purified receptor protein, or cells or membrane preparations bearing the receptor, may be used to generate monoclonal or polyclonal antibodies specific for the given receptor, which antibodies can be employed in assays for detecting the presence or the amount of such receptor in biological samples such as serum or tissue biopsies. Some tumors, including certain ocular melanomas as well as tumors of the female genital tract, are susceptible to the antiproliferative effects of MIS (Donahoe et al., Science 205:913–915, 1979; Donahoe et al., Ann. Surg. 194:472–480, 1981; Fuller et al., J. Clin. Endo. Metab. 54:1051–1055, 1982; Fuller et al., Gynecol. Oncol. 22:135–148, 1985; Chin et al., Cancer Res. 51:2101–2106, 1991; Parry et al., Cancer Res. 52:1182–1186, 1992; and Donahoe, U.S. Ser. No. 683,966, herein incorporated by reference), and it is postulated that the growth of other tumor types may be similarly reduced by inhibin or BMP. The antibodies of the invention would therefore be useful for identifying candidate tumors likely to respond to therapy with MIS, inhibin, BMP, or agonists or antagonists thereof. The receptor polypeptides of the invention, and their respective antibodies, could be used as receptor agonists or antagonists in the management of relevant clinical disorders. The antibodies can also be used as the targeting means for directing cytotoxic agents to cells (such as tumor cells) bearing the given receptor. Examples of cytotoxic agents commonly used in such applications include, for example, polypeptide toxins such as diphtheria toxin, Pseudomonas exotoxin A, ricin, and gelonin, or defined toxic portions thereof; radioisotopes; and agents such as cisplatinum, adriamycin, bleomycin, and other therapeutic cytotoxins. Methods for making such immunotoxins are well known to those of ordinary skill in the art, and may include genetic engineering technology as well as chemical-based techniques.

Purified receptor protein, or transformed cells expressing the receptor protein, can be used to screen candidate drugs for their ability to block or enhance the binding of MIS, inhibin, or BMPs to their respective receptors. This could be accomplished by means of a competition assay using, for example, labelled ligand and excess candidate drug. Inhibitors of MIS ligand/receptor binding would potentially be useful for preventing or alleviating respiratory distress syndrome in newborns (Donahoe et al., U.S. Ser. No. 416,235, now abandoned, herein incorporated by reference). Substances which act as inhibitors of inhibin/receptor binding could be used for treatment of infertility: for example, the extracellular domain of a soluble inhibin receptor can act as an inhibin antagonist, thereby increasing the level of FSH in infertile patients with low FSH. Inhibitors of BMP/receptor binding (such as the extracellular domain of a BMP receptor) could be used in a similar fashion to enhance the action of bone-specific trophic factors.

Recombinant forms of the MIS receptor, inhibin receptor, or BMP receptors, or ligand-binding portions thereof, can be used to measure the amount of ligand (MIS, inhibin, or one of the BMPs) present in a biological sample. This could be accomplished, for example, by means of a sandwich assay utilizing the recombinant receptor protein fixed to a solid support, and labelled anti-ligand antibody. Where the ligand being measured is MIS, it may be desireable to include plasmin or an MIS-specific protease in the assay, in order to permit the cleavage of any holo MIS present in the sample into its receptor-binding form. The recombinant receptors of the invention would also be useful as a means for assaying receptor binding by analogs of MIS, inihibin, and the BMPs, in order to develop analogs with an enhanced affinity for the given receptor. Those analogs which are capable of stimulating a signal through the receptor can then be used in MIS, inhibin or BMP replacement therapy, while those analogs which bind but do not activate the given receptor will be useful as inhibitors of the natural ligand.

The receptors of the invention may also have therapeutic applications. Where a given condition, such as respiratory distress syndrome in newborns, is attributable to an overabundance of MIS in a given tissue, exposure of that tissue to recombinant MIS receptor protein, or a soluble, MIS-binding fragment thereof, provides a means for reducing the amount of MIS available for binding to natural receptors in the tissue and thereby alleviating the underlying cause of the condition. Similarly, a soluble, inhibin-binding fragment of the inhibin receptor would be useful, as discussed above, for increasing the level of FSH in patients with infertility attributable to abnormally low FSH levels. A soluble, BMP-binding fragment of a BMP receptor could be utilized in an assay to measure the amount of a particular BMP present in a biological sample: for example, to determine whether BMP supplemental therapy would be called for in a given case of retarded bone growth or repair of traumatic bone injuries or deficiency due to removal of bone in surgery for a malignancy or other deformities. Such soluble receptor fragments can be readily produced by genetically engineering the receptor cDNAs of the invention to delete those portions encoding the largely hydrophobic putative transmembrane regions, but leaving intact the sequences encoding the putative extracellular domains. Such methods are well known in the art. One example of a soluble fragment of MISR1 would include most or all of amino acids 1 to 510 of the sequence shown in FIG. 1 (SEQ ID NO: 14), but would not include amino acids 121 to 138. Alternatively, a given soluble receptor fragment may be produced by proteolytic treatment of naturally occurring or recombinant membrane-bound MIS or inhibin receptors. Such soluble fragments can be assayed for their ability to bind to ligand by the use of radiolabelled ligand or ligand fixed to affinity matrix.

Deposit

Under the terms of the Budapest Treaty on the International Recognition of the Deposit of Microorganisms for the Purpose of Patent Procedure, a deposit of plasmids misr1, misr2A, misr2B, misr3, and misr4 has been made with the American Type Culture Collection (ATCC) of Rockville 12301 Parklawn Drive, Md. USA, where the deposit was given Accession No. 75213.

Applicants' assignee, the General Hospital Corporation, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. §122. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

Experimental Data

Four novel membrane serine/threonine kinase receptor cDNAs from the rat urogenital ridge were cloned and characterized as described below.

Polymerase chain reaction (PER) using consensus primers.

The DNA sequence of the cDNA encoding a murine activin receptor (Mathews and Vale, Cell 65:973–982, 1991) was compared to that of certain related cDNAs: human and porcine TGF-β type II receptor (Lin et al., Cell 68:775–785, 1992) and the daf-1 receptor of C. elegans (Georgi et al., Cell 61:635–645, 1990), and two highly conserved regions defined. These two regions formed the basis for the design of two degenerate oligonucleotides:

| | |
|---|---|
| 5'-GTGGCCGT(G/C)AA(A/G)AT(C/T)TT-3' | (SEQ ID NO: 10) |
| and 5'-GAC(T/C)TCTGG(G/A)GCCAT(G/A)TA-3' | (SEQ ID NO: 11). |

The oligonucleotides were synthesized with an Applied Biosystems 391 DNA synthesizer, and used as primers for polymerase chain reaction (PCR)-based selection from a 14.5 day rat urogenital ridge COS cell expression cDNA library. PCR was carried out in a 50 µl reaction mixture containing about 1 µg of cDNA plasmid; 10 mMTris-HCl, pH 8.3; 50 mM KCl; 5 mM MgCl$_2$; 0,001% gelatin; 250 µM each of dATP, dCTP, dGTP, and dTTP; 1 unit of Taq polymerase (Perkin-Elmer Cetus); and 50 pmol each of the above oligonucleotides. Thirty cycles of PCR (consisting of denaturation at 94° C. for 1 min; annealing at 37° C. for 1 min; and elongation at 72° C. for 1 min) were performed. The PCR products were separated on a 1.5% agarose gel and a predicted 400–500 bp DNA fragment was sliced out and purified by Gene-clean™. The purified PCR product was blunt-ended with Klenow fragment and phosphorylated with T4 polynucleotide kinase. The final PCR fragment was ligated, using T4 DNA ligase, with plasmid pGEM7Z(+) vector which was digested with Sma I and dephosphorylated. The ligation mixture was incubated at room temperature for 3 hours, and then transformed into bacteria HB 101 by electroporation. Bacterial colonies resistant to ampicillin were selected overnight on 1.5% agar plates containing 50 µg/ml ampicillin. Individual colonies were picked and grown in 5 ml of LB broth, and plasmids were isolated according to a standard plasmid mini-prep protocol. The plasmid DNA was then sequenced with bacterial phage promoter SP6 and T7 primers using Sequenase (USB). Four clones containing PCR fragments encoding portions of four novel polypeptides (putative serine/threonine kinases) were designated pGEM7-Misr1, pGEM7-Misr2, pGEM7-Misr3 and pGEM7-Misr4, respectively. In addition, cDNAs encoding portions of TGF-beta receptor and activin receptor were isolated during this procedure; these were designated pGEM7-tgfb and pGEM7-actr, respectively.

cDNA Library Synthesis

Approximately 450 urogenital ridges and their adjacent gonads were collected from 24 litters of 14.5–15 day gestational age fetal rats, and flash frozen in liquid nitrogen. RNA was then extracted from this tissue by homogenization in 50% guanidinium thiocyanate/14.5% lithium chloride/ 0.2% β-mercaptoethanol, centrifugation through 5.7M cesium chloride (50 k rpm for 2 hours), and precipitation with NaOAc and ethanol. Poly A+ RNA was further obtained by oligo dT—cellulose chromatography of 620 μg total RNA. Twenty μg of this poly A+ RNA was subsequently used for first strand cDNA synthesis, using 4 μl of reverse transcriptase (RT-XL, Life Sciences), 2.5 μl of 20 mM ultrapure dNTP, 1 μl of oligo dT (Collaborative Research, 5 μg/μl) as primer, 20 μL of RT1 buffer, 1 μL 1.0M DTT, and 2 μl of placental RNase inhibitor (Boehringer, 36 U/μl) in a total volume of 100 μl, incubated for forty-five minutes at 42° C. The second strand synthesis reaction, which employed 5 μl of DNA polymerase I (Boehringer, 5 U/μl) and 2 μl of RNase H (BRL, 2 U/μl), was performed for one hour at 15° C. followed by one hour at 22° C., prior to termination with 20 μl of 0.5M EDTA, pH 8.

The cDNA mixture was then phenol extracted and ethanol precipitated, and then ligated to non-self-complimentary BstX1 linkers (Invitrogen) using 1 μl of T4 DNA ligase (NE Biolabs, 400 U/μl), in a volume of 50 μl incubated at 15° C. overnight. Small cDNA and free linkers were removed by centrifugation through a 5–20% KOAc gradient. Fractions of the gradient that contained cDNA larger than one kilobase were ethanol precipitated with linear polyacrylamide and pooled. After test ligations had determined the optimal ratios, the cDNA was ligated into the COS cell expression vector CDM8, previously digested with BstX1. The cDNA/ vector products were electroporated (BioRad Gene Pulser) into competent E. coli MC1061/p3 cells, which were then grown on 20 LB/ampicillin bacterial plates. The resulting cDNA library contained 1×10⁶ individual clones, with an average insert size of 1.5–2.0 kb. Maxiprep plasmid DNA (total yield 1.9 mg) was subsequently obtained from a "pooled" overnight liquid culture of these clones.

A lambda Zap II library was constructed by Stratagene using 20 μg of urogenital ridge mRNA.

Cloning of the full-length CDNAs for Misr1, Misr3 and Misr4, and two partial cDNAs for Misr2

The plasmid DNA of each of pGEM7-misr1, pGEM7-misr2, pGEM7-misr3, and pGEM7-misr4 was prepared in large quantities according to a standard plasmid large-prep protocol. The inserts of individual clones were excised out of the plasmid vector with restriction enzymes Eco RI and Bam HI. The inserts were then gel-separated and purified with Gene-clean™. The purified DNA inserts were labeled with ³²P-dCTP using a random-priming technique, to a specific activity of greater than 1×10⁹ cpm/μg. The individually labeled DNA probes were then used to screen a 14.5 day rat urogenital ridge lambda ZAP II cDNA library made by Stratagene. Positive clones were plaque-purified and the inserts were excised into plasmid pBluescript I SK according to Stratagene's protocol. Full-length clones were sequenced with Sequenase on both strands by synthesizing internal 16-17 oligonucleotide sequencing primers. The full-length DNA coding sequence of misr1 (SEQ ID NO: 1) and the amino acid sequence of its encoded polypeptide (referred to as MISR1; SEQ ID NO: 14) are shown in FIG. 1. The full coding sequence of misr2A/misr2B is shown in FIG. 2 (SEQ ID NO: 2), where the overlap between the two cloned sequences is indicated. The full length polypeptide encoded by a DNA sequence resulting from the ligation of appropriate portions of misr2A and misr2B to produce a single, full-length coding sequence is also shown in FIG. 2; this full-length polypeptide is referred to herein as MISR2 (SEQ ID NO: 15). Full-length sequences of clones misr3 and misr4 are shown in FIG. 3 (SEQ ID NO: 3) and FIG. 4 (SEQ ID NO: 4), respectively. The full-length polypeptide encoded by misr3 is termed MISR3 (shown in SEQ ID NO: 16), while the full-length polypeptide encoded by misr4 is termed MISR4 (shown in SEQ ID NO: 17). Each sequence was compared to sequences in the GenBank database, and found to be unique. Misr1 (SEQ ID NO: 1) is believed to encode an isoform of the rat MIS receptor, while misr2A/ misr2B (SEQ ID NO: 2), misr3 (SEQ ID NO: 3), and misr4 (SEQ ID NO: 4) are believed to encode monomeric isoforms of the rat inhibin receptor and/or BMP receptor.

Each putative receptor of 501–509 amino acid residues possesses the characteristic domain features of the TGF-β receptor superfamily, including a hydrophobic signal peptide of 19–23 residues (von Heijne, Biochim. Biophys. Acta 947:307, 1988); an extracellular, cysteine-rich, hydrophilic, ligand-binding domain of 100–150 residues, a hydrophobic single transmembrane domain of 23–25 residues (Kyte et al, J. Mol. Biol. 157:105, 1982), an intracellular serine/threonine kinase domain of approximately 300 residues, and a short serine/threonine rich tail. Sequence alignment with the TGF-β and activin type II receptors and daf-1 reveals greatest the similarity between their intracellular domains, including conservation of 22 amino acid residues that are characteristic of the serine/threonine subfamily of protein kinases (Hanks, Meth. Enzymol. 200:38, 1991). All such kinases, including members of the TGF-β receptor family and MISR1-MISR4, have 12 subdomains of highly conserved residues. For example, $GXGXXGXVX_{11-28}K$, conserved in subdomains I and II and thought to form an ATP binding site, aligns well in MISR1–MISR4 as $GKGR(Y/F)GEVX_{12}K$ (SEQ ID NOs: 12 and 13). Subdomains VIB and VIII are key regions which determine tyrosine and serine/threonine kinase specificity; in each of MISR1–MISR4, these domains are more homologous to the serine/threonine motif than to the tyrosine sequence (Hanks et al., Science 241:42–52, 1988).

In situ Hybridization

Plasmids pGEM7-Misr1, pGEM7-Misr2, pGEM7-Misr3, and pGEM7-Misr4 were linearized with appropriate restriction enzymes. Antisense or sense RNA probes labelled with [³⁵S]-UTP were generated by transcription of the linearized plasmid DNA using the Riboprobe Gemini System II (Promega Biotech) with SP6 or T7 RNA polymerases.

Tissue sections were postfixed in 4% paraformaldehyde in 0.1M phosphate buffer, pH 7.4, for 5 minutes at room temperature, then rinsed twice in PBS. The sections were rinsed briefly with 0.1M triethanolamine-HCl, pH 8.0, and then treated with 0.25% acetic anhydride in 0.1M triethanolamine-HCl, pH 8.0, for 10 min. at room temperature. The sections were rinsed twice in 2× sodium chloride/sodium citrate (SCC), then dehydrated in increasing concentrations of ethanol, delipidated in chloroform, rehydrated, and air dried for 30 min. at room temperature. Sections were hybridized under coverslips for 15 hours at 55° C. using ³⁵S-labelled sense or antisense probe (2×10⁷ cpm/ml) in 50% formamide, 600 mM NaCl, 10 mM Tris-HCl (pH 7.5), 0.02% Ficoll, 0.02% bovine serum albumin, 0.02% polyvinylpyrrolidone, 1 mM EDTA, 0.01% salmon testis DNA, 0.05% total yeast RNA, 0.005% yeast tRNA, 10% dextran sulfate, 0.1% SDS, 0.1% sodium thiosulfate, and 100 mM DTT. After hybridization, slides were immersed in 2× SSC for 30 min. at room temperature, and floated off the coverslips. The slides were first treated with RNase A (20 mg/ml) in RNase buffer (0.5M NaCl, 10 mM Tris-HCl, pH 8.0, 1.0 mM EDTA) for 30 min. at 37° C. and washed in the same buffer for 30 min. at 37° C. The slides were then washed in 2× SSC for 1 hour at 50° C., 0.2× SSC for 1 hour at 55° C., 0.2× SSC for 1 hour at 60° C., then dehydrated sequentially in 70%, 80%, and 95% ethanol containing 300 mM ammonium acetate, and absolute ethanol before air drying. To detect autoradiographic silver grains, the slides were dipped into Kodak NTB-2 nuclear track emulsion diluted 1:1 with 0.1% Aerosol 22 (Sigma) at 42° C., dried gradually in a high humidity chamber for 2 hours, then exposed at 4° C. for 7–14 days. The slides were developed in Kodak D19 for 2 min. at 16° C., rinsed in deionized water for 30 sec., fixed in Kodak fixer for 5 min., then washed in deionized water and stained with hematoxylin. Sections were examined using bright and darkfield illumination.

To identify potential ligands for MISR1–MISR4 binding studies, in situ hybridization was performed with 13 to 16-day fetal urogenital ridge and fetal, peripubertal, and adult gonads (FIGS. 6A–6F). Remarkably, misr1 was the only clone to localize specifically to 14.5 to 15-day fetal male Mullerian duct mesenchyme, but not to the adjacent Wolffian duct or gonad or to 13 or 16-day Mullerian tissue. This was a consistent finding using misr1 riboprobes derived from either the 3' conserved domain or the 5' extracellular region, making cross-hybridization with homologous receptors unlikely. In addition, misr1 message localized to oocytes of preantral and antral follicles of the peripubertal and adult ovary. Because the expression and ontogeny of misr1 mRNA is consistent with both the known site (Trelstad et al., Develop. Biol. 92:27–40, 1982; Tsuji et al., Endocrinology 131:1481–1488, 1992) and timing (Picon, Arch. Anat. Micro. Morphol. Exp. 58:1–19, 1969) of MIS action in the urogenital ridge, as well as the cycling adult ovary (Takahashi et al., Molec. Cell. Endocr. 47:225–234, 1986; Ueno et al., Endocrinology 125:1060–1066, 1989), MISR1 is the best candidate for the rat MIS receptor. MISR2 mRNA, on the other hand, localized in a heterogeneous pattern to seminiferous tubules of pubertal and adult testes, but was not detectable within the fetal or adult ovary (FIGS. 6E and 6F). Both MISR1 and MISR2 transcripts were also observed in the postnatal female anterior pituitary and hippocampus (data not shown), but their cellular localization has not been clearly delineated.

Northern Analysis

Northern analysis of a variety of fetal and adult rat tissues was performed to determine both the tissue and temporal specificity of expression of RNA corresponding to each of the four newly identified receptor clones. Total RNA was extracted by a modification of the method of Chirgwin using guanidinium thiocyanate/lithium chloride; RNA quantification was by spectrophotometric analysis and ethidium bromide staining of test gels. Ten µg of total RNA (or in selected cases, 1 µg of poly-A+ RNA) were loaded in each lane of 1.5% Morpholinopropanesulfonic acid-formaldehyde agarose gels, electrophoresed at 5 V/cm, transferred to Biotrans nylon membranes (ICN Biomedicals, Irvine, CA) by capillary action in 25 mM sodium phosphate, and then fixed by UV irradiation.

Membranes were prehybridized in plaque screen buffer (0.05M Tris-Cl, 0.1% Na pyrophosphate, 1M NaCl, 0.2% polyvinylpyrrolidone, 0.2% Ficoll, 0.2% BSA, 1% SDS) containing 0.1 mg/ml tRNA for 2 hours at 65° C. Membranes were then hybridized with one of the four randomly primed, $^{32}$P-labeled receptor cDNA clones, which varied in length from 0.5 to 3.0 kb. Overnight hybridization was performed with $1\times10^6$ cpm/ml in plaque screening buffer containing 0.1 mg/ml tRNA. All hybridizations and washes were done at 65° C.; 30 mM NaCl/3.0 mM Na citrate/0.5% SDS was the most stringent wash. Autoradiographic exposures were for 3–10 days.

Figures 7A, 7B:
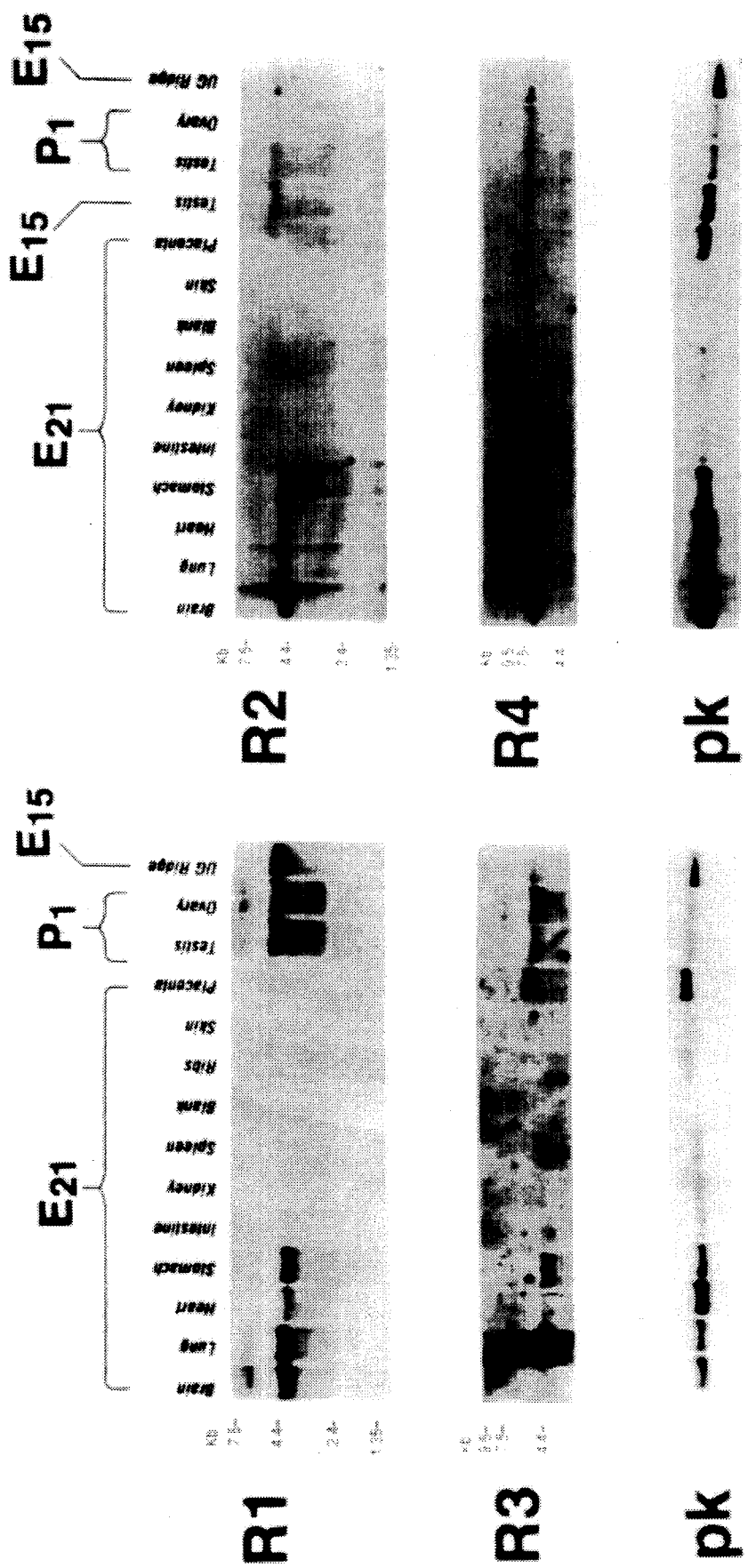

As shown in FIGS. 7A and 7B, mRNA transcripts of 4.0 kb (misr1), 4.4 and 1.5 kb (misr2A/misr2B), 4.4 kb (mist3), and 6 kb (misr4) were detected in 15-day (E15) fetal urogenital ridge tissue and postnatal day 1 (P1) testis and ovary. Similar levels of expression were found for each clone in pubertal and adult gonads. misr1, misr2, and misr4 message was also abundant in the 21-day (E21) fetal brain, with misr1 mRNA persisting in the adult female brain (data not shown). Interestingly, all four of these mRNAs are present in the E21 lung (particularly misr3 and misr4) and persist there to adulthood (data not shown). Transcripts for misr1 and misr2, and less so for misr3, were detected in other E21 tissues such as the lung, heart, and stomach, suggesting a more universal distribution of these receptors than anticipated.

As illustrated in FIGS. 8 and 9, the misr1 (MIS receptor) probe hybridized to mRNA from testes, ovary, brain, and pituitary, while the misr2 (inhibin receptor) probe hybridized with testicular RNA in a distinctive temporal pattern. Misr2 probe was also found to hybridize to ovarian and brain tissue (data not shown). These results are consistent with the conclusion that misr1 encodes the rat MIS receptor, while misr2A/2B together encode the rat inhibin receptor.

Holo RhMIS Purification

Recombinant human MIS (rhMIS) purification by immunoaffinity chromatography from conditioned media of Chinese hamster ovary cells transfected with human MIS gene is as follows. Media were collected every 3–4 days from bioreactor cultures (Epstein et al., In Vitro Cell. Der. Biol. 25:213–216, 1989), and stored at −20° C. until use. A 5 ml immunoaffinity column was constructed using approximately 50 mg of the protein A-Sepharose (Sigma Chemical Co., St. Louis, Mo.) purified mouse monoclonal anti-human rhMIS antibody (Hudson et al., J. Clin. Endocrinol. Metab. 70:16–22, 1990) covalently attached to Affigel-10 agarose resin (BioRad Laboratories, Richmond, Calif.). The column was equilibrated with 100 ml of 20 mM 4-(2-hydroxyethyl)-1-piperazineethanesulfonic acid (Hepes), pH 7.4, and 200 ml of concentrated medium loaded after filtration through Whatman #4 paper at 1 column volume/h at 4° C. After loading, the column was washed with 20 mM Hepes, pH 7.4, until the absorbance at 280 nm returned to baseline (60–100 ml).

RhMIS was eluted using 1M acetic acid in 20 mM Hepes, pH 3.0, after a one column volume pre-elution wash containing 0.5M NaCl, 1 mM EDTA, 0,001% nonidet P-40 (NP-40, Sigma Chemical Co., St. Louis, Mo.), 20 mM Hepes, pH 7.4. The majority of the rhMIS eluted in a single 2 ml fraction, which was immediately neutralized with NaOH to a pH between 7.0 and 7.4. The acid-eluted immunoaffinity-purified (IAP) fractions were dialyzed overnight versus 0.02M Hepes, 0,001% NP-40, pH 7.4. The resulting samples were analyzed for total protein by the Bradford method (Bradford, Anal. Biochem. 72:248–254, 1976) and for rhMIS concentrations by an enzyme-linked immunosorbent assay (Hudson et al., J. Clin. Endocrinol. Metab. 70:16–22, 1990). They were further examined by polyacrylamide gel electrophoresis (Weber et al., J. Biol. Chem. 244:4406–4412, 1969) and activity determined in an in vitro Müllerian duct regression bioassay.

Purification of the carboxyl-terminus of rhMIS

Immunoaffinity purified rhMIS (1.1–1.5 mg in 2.5 ml of 20 mMHepes buffer, pH 7.4) was incubated with plasmin (EC 3.4.21.7, Sigma Chemical Co., St. Louis, Mo.) at a ratio of 20 to 25:1 rhMIS to plasmin w:w for 2 hr at room temperature as previously described (Pepinsky et al., J. Biol. Chem. 263:18961–18964, 1988). The preparation was then placed onto a 2.5×16 cm P-100 polyacrylamide column (BioRad Laboratories, Richmond, Calif.) equilibrated at 4° C. with 1.0M acetic acid in 20 mMHepes at pH 3.0. Protein was eluted in 0.54 ml fractions at a flow rate of approximately 2.0 ml/hr. Ten microliter aliquots were analyzed for protein by the Bradford method (Bradford, Anal. Biochem. 72:248–254, 1976). Two peaks of protein, termed A and B, elute from this column. These peaks were pooled separately, frozen in liquid nitrogen, and concentrated by lyophilization in a Savant Speed Vac apparatus. The resulting pools were dissolved in either 20 mMHepes, pH 7.4, or 0.3M sodium phosphate, pH 7.4, so that a final protein concentration of 1 mg/ml was achieved. Elution buffer in volumes similar to those of the pools was also lyophilized and dissolved in buffer as above to serve as controls for the rhMIS bioassays.

Rh MIS Bioassay

The standard organ culture bioassay for MIS was performed as described (Donahoe et al., Biol. Reprod. 16:238–243;MacLaughlin et al., Methods in Enzymology 198:358–369, 1991). Briefly, 14½ day female fetal rat urogenital ridges were placed on agar-coated stainless steel grids above fortified CMRL 1066 medium (GIBCO/BRL, Gaithersburg, Md.) containing female fetal (and therefore MIS-free) calf serum (Necklaws et al., Endocrinology 118:791–796, 1986) and testosterone at $10^{-9}$M, to enhance the Wolffian duct for direct comparison of the Müllerian duct in each tissue section. RhMIS protein samples of 0.5 to 8.0 µg each, or buffer controls, were added in serum containing CMRL medium after sterile filtration in that solution through a 0.22 µm Millex GV membrane. Control studies using carboxyl-terminal rhMIS radiolabeled with $I^{125}$ by a standard technique (Hunter, Proc. Soc. Exp. Biol. Med. 133:989–992, 1970) demonstrated no loss of the protein to this filter. After incubation for 3 days in humidified 5% $CO_2$ at 37° C., the specimens were fixed in 15% formalin, embedded in paraffin, and 8 µm sections of the cephalic end stained with hematoxylin and eosin. The sections were then ranked from grade 0 (no regression) to grade 5 (complete regression), by two experienced observers. One unit of activity is defined as causing a 1 grade increase in Müllerian duct regression. Data were compared by Student's t-test for significant differences among groups.

Radioisotope labelling of ligand

Iodination of both MIS and inhibin carboxyl terminal fragments is performed with $^{125}I$ Na and chloramine-T. One to five µg of protein is suspended in 0.3M sodium phosphate buffer, pH 7.5, and radioisotope then added at a ratio of 1mCi:5 µg. Three serial additions of chloramine-T solution are next performed, with a final chloramine-T to protein ratio of 1:7 and a total reaction time of 4.5 minutes. The reaction is terminated with saturated potassium iodide solution containing 0.1% BSA; free isotope is then separated from radiolabeled ligand by size exclusion chromatography. Estimated specific activities of $50$–$70\times10^6$ cpm/µg have been obtained for both ligands using this method.

Other embodiments are within the following claims.

---

What is claimed is:

1. Isolated DNA comprising a strand having
   (a) a DNA sequence which encodes a naturally occuring Müllerian Inhibitory Substance (MIS) receptor, wherein a DNA having said sequence hydridizes under high stringency conditions with 50 nucleotide portion of the antisense strand of the coding region of misr1 cDNA (SEQ ID No:1);
   (b) a DNA sequence which is a degenerate variant of (a); or
   (c) a DNA sequence complementary to the full length of (a) or (b).

2. The isolated DNA of claim 1, wherein said receptor is a mammalian protein.

3. The isolated DNA of claim 1, wherein said receptor is a human protein.

4. The isolated DNA of claim 1, wherein said receptor is a rat protein.

5. The isolated DNA of claim 4, wherein said receptor has the amino acid sequence of MISR1 (SEQ ID NO: 14).

6. The isolated DNA of claim 1, wherein said DNA having said receptor-encoding sequence also hybridizes under high stringency conditions with a nucleic acid complementary to the full length of the coding sequence of misr1 (SEQ ID NO: 1).

7. The isolated DNA of claim 1, wherein said strand has the sequence of misr1 cDNA (SEQ ID NO:1).

8. Isolated single-stranded DNA consisting of the sense or antisense strand of a DNA according to claim 1.

9. The isolated DNA of claim 1, wherein said sequence which encodes said receptor is under the transcriptional control of a heterologous promoter.

10. A vector comprising the isolated DNA of claim 1.

11. The vector of claim 10, wherein said vector is a viral nucleic acid.

12. A cultured cell comprising the isolated DNA of claim 1.

13. The cell of claim 12, wherein said cell is a eukaryotic cell.

14. The cell of claim 12, wherein said cell is capable of expressing said receptor.

15. A method of expressing a receptor polypeptide, comprising culturing the cell of claim 11 funder conditions that permit expression of said isolated DNA to produce said receptor.

16. The method of claim 15, wherein said receptor is a human MIS receptor.

17. The method of claim 15, wherein said cell a eukaryotic cell.

18. A substantially pure nucleic acid at least 50 nucleotides in length comprising a strand which
   (a) hybridizes under high stringency conditions to either the sense or the antisense stand of the coding region of misr1 (SEQ ID NO: 1); and
   (b) has a sequence which encodes, or is antisense to a sequence encoding, part or all of a naturallyoccurring MIS receptor.

19. The nucleic acid of claim 18, wherein said nucleic acid encodes all of said receptor.

20. The nucleic acid of claim 19, wherein said nucleic acid is RNA.

21. The nucleic acid of claim 18, wherein said receptor is a human MIS receptor.

22. The nucleic acid of claim 21, wherein said nucleic acid encodes all of said receptor.

23. The nucleic acid of claim 22, wherein said nucleic acid is RNA.

24. Isolated DNA at least 50 nucleotides in length comprising a strand having a DNA sequence selected from the group consisting of
(a) a fragment of a sequence encoding a naturally occurring MIS receptor, wherein an oligonucleotide antisense to said fragment hybridizes under high stringency conditions with the coding sequence of misr1 cDNA (SEQ ID NO: 1);
(b) a degenerate variant of (a); or
(c) a sequence complementary to the full length of (a) or (b).

25. The isolated DNA of claim 24, wherein said fragment is at least 100 nucleotides in length.

26. A substantially pure single- or double-stranded nucleic acid at least 20 nucleotides in length consisting of a segment of a cDNA encoding a naturally occurring human MIS receptor, wherein said cDNA comprises a strand which hybridizes under high stringency conditions with a 50 nucleotide portion of the sense or antisense strand of the coding region of misr1 (SEQ ID NO: 1).

27. A substantially pure nucleic acid at least 20 nucleotides in length consisting of a segment of the coding sequence of misr1 (SEQ ID NO: 1).

* * * * *

UNITED STATES PATENT AND TRADEMARK OFFICE
CERTIFICATE OF CORRECTION

PATENT NO. : 5,547,854
DATED : August 20, 1996
INVENTOR(S) : Donahoe et al.

It is certified that error appears in the above-identified patent and that said Letters Patent is hereby corrected as shown below:

Title page,
Item [56], References Cited, OTHER PUBLICATIONS, delete "Cohen-Maguenauer et al." and insert -- Cohen-Haguenauer et al. -- delete "Hagg et al." and insert -- Haqq et al. -- delete "Knebelmenn et al." and insert -- Knebelmann et al. -- delete "Taketo et al., Development Biology 166:386-395, 1991" and insert -- Taketo et al., Developmental Biology 146:386-395, 1991 --

Column 6,
Line 59, delete "A7" and insert -- 7A --

Column 11,
Line 63, delete "A7" and insert -- 7A --

Column 11,
Line 63, delete "of Rockville 12301 Parklawn Drive, Md." and insert -- of 12301 Parklawn Drive, Rockville, Md. --

Column 45,
Line 38, delete "wherein a DNA having said sequence" and insert -- wherein a nucleic acid having said sequence --

Column 46,
Line 53, delete "antisense stand" and insert -- antisense strand --
Line 56, delete "naturallyoccurring" and insert -- naturally occurring --

Column 46,
Line 39, delete "with 50" and insert -- with a 50 --
Line 43, delete "funder"and insert -- under --

UNITED STATES PATENT AND TRADEMARK OFFICE
CERTIFICATE OF CORRECTION

PATENT NO. : 5,547,854
DATED : August 20, 1996
INVENTOR(S) : Donahoe et al.

It is certified that error appears in the above-identified patent and that said Letters Patent is hereby corrected as shown below:

Column 46, (cont'd,)
Line 53, delete "antisense stand" and insert -- antisense strand --
Line 56, delete "naturallyoccurring" and insert -- naturally occurring --

Signed and Sealed this

Nineteenth Day of April, 2005

JON W. DUDAS
*Director of the United States Patent and Trademark Office*

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 1530
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
ATG  GTC  GAT  GGA  GCA  ATG  ATC  CTT  TCT  GTG  CTA  ATG  ATG  ATG  GCT  CTC      48
Met  Val  Asp  Gly  Ala  Met  Ile  Leu  Ser  Val  Leu  Met  Met  Met  Ala  Leu
 1              5                        10                       15

CCT  TCC  CCG  AGT  ATG  GAA  GAT  GAG  GAG  CCC  AAG  GTC  AAC  CCG  AAG  CTT      96
Pro  Ser  Pro  Ser  Met  Glu  Asp  Glu  Glu  Pro  Lys  Val  Asn  Pro  Lys  Leu
              20                        25                       30

TAC  ATG  TGT  GTG  TGT  GAG  GGC  CTC  TCC  TGC  GGG  AAC  GAG  GAC  CAC  TGT     144
Tyr  Met  Cys  Val  Cys  Glu  Gly  Leu  Ser  Cys  Gly  Asn  Glu  Asp  His  Cys
         35                       40                       45

GAG  GGC  CAG  CAG  TGT  TTT  TCC  TCC  CTG  AGC  GTC  AAT  GAT  GGC  TTC  CGC     192
Glu  Gly  Gln  Gln  Cys  Phe  Ser  Ser  Leu  Ser  Val  Asn  Asp  Gly  Phe  Arg
     50                       55                       60

GTC  TAC  CAG  AAG  GGC  TGC  TTT  CAG  GTC  TAT  GAG  CAG  GGG  AAG  ATG  ACG     240
Val  Tyr  Gln  Lys  Gly  Cys  Phe  Gln  Val  Tyr  Glu  Gln  Gly  Lys  Met  Thr
 65                       70                       75                       80
```

| | | | | | | | | | | | | | | | | |
|---|---|---|---|---|---|---|---|---|---|---|---|---|---|---|---|---|
| TGT | AAG | ACC | CCG | CCG | TCG | CCT | GGC | CAG | GCT | GTG | GAG | TGC | TGC | CAA | GGG | 288 |
| Cys | Lys | Thr | Pro 85 | Pro | Ser | Pro | Gly | Gln 90 | Ala | Val | Glu | Cys | Cys 95 | Gln | Gly | |
| GAC | TGG | TGC | AAC | AGG | AAC | GTC | ACG | GCC | CGG | CTG | CCC | ACT | AAA | GGG | AAA | 336 |
| Asp | Trp | Cys | Asn 100 | Arg | Asn | Val | Thr | Ala 105 | Arg | Leu | Pro | Thr | Lys 110 | Gly | Lys | |
| TCC | TTC | CCT | GGA | TCG | CAG | AAC | TTC | CAC | CTG | GAA | GTT | GGC | CTT | ATC | ATC | 384 |
| Ser | Phe | Pro 115 | Gly | Ser | Gln | Asn | Phe | His 120 | Leu | Glu | Val | Gly | Leu 125 | Ile | Ile | |
| CTC | TCC | GTG | GTG | TTT | GCG | GTA | TGC | CTT | TTC | GCT | TGC | ATC | CTT | GGC | GTT | 432 |
| Leu | Ser 130 | Val | Val | Phe | Ala | Val 135 | Cys | Leu | Phe | Ala | Cys 140 | Ile | Leu | Gly | Val | |
| GCT | CTC | AGG | AAG | TTT | AAA | AGG | CGC | AAT | CAA | GAG | CGC | CTG | AAC | CCC | AGA | 480 |
| Ala 145 | Leu | Arg | Lys | Phe 150 | Lys | Arg | Arg | Asn | Gln 155 | Glu | Arg | Leu | Asn | Pro 160 | Arg | |
| GAC | GTG | GAG | TAC | GGT | ACT | ATC | GAA | GGG | CTC | ATC | ACC | ACC | AAC | GTC | GGA | 528 |
| Asp | Val | Glu | Tyr | Gly 165 | Thr | Ile | Glu | Gly | Leu 170 | Ile | Thr | Thr | Asn | Val 175 | Gly | |
| GAT | AGC | ACT | CTA | GCG | GAA | TTA | CTA | GAT | CAC | TCG | TGT | ACA | TCA | GGA | AGT | 576 |
| Asp | Ser | Thr | Leu 180 | Ala | Glu | Leu | Leu | Asp 185 | His | Ser | Cys | Thr | Ser 190 | Gly | Ser | |
| GGC | TCC | GGT | CTT | CCT | TTT | CTG | GTA | CAG | AGA | ACT | GTG | GCT | CGA | CAG | ATA | 624 |
| Gly | Ser | Gly 195 | Leu | Pro | Phe | Leu | Val 200 | Gln | Arg | Thr | Val | Ala 205 | Arg | Gln | Ile | |
| ACC | CTG | TTG | GAG | TGT | GTC | GGG | AAG | GGC | CGG | TAT | GGA | GAA | GTG | TGG | AGG | 672 |
| Thr | Leu 210 | Leu | Glu | Cys | Val | Gly 215 | Lys | Gly | Arg | Tyr | Gly 220 | Glu | Val | Trp | Arg | |
| GGC | AGC | TGG | CAA | GGC | GAA | AAT | GTT | GCT | GTG | AAG | ATC | TTC | TCC | TCC | CGT | 720 |
| Gly | Ser | Trp | Gln | Gly 230 | Glu | Asn | Val | Ala | Val 235 | Lys | Ile | Phe | Ser | Ser 240 | Arg | |
| GAT | GAG | AAG | TCG | TGG | TTC | AGG | GAG | ACA | GAA | TTG | TAC | AAC | ACG | GTG | ATG | 768 |
| Asp | Glu | Lys | Ser | Trp 245 | Phe | Arg | Glu | Thr | Glu 250 | Leu | Tyr | Asn | Thr | Val 255 | Met | |
| CTG | AGG | CAT | GAG | AAT | ATC | TTA | GGT | TTC | ATT | GCT | TCA | GAC | ATG | ACC | TCT | 816 |
| Leu | Arg | His | Glu 260 | Asn | Ile | Leu | Gly | Phe 265 | Ile | Ala | Ser | Asp | Met 270 | Thr | Ser | |
| AGA | CAC | TCC | AGT | ACC | CAG | CTG | TGG | CTC | ATT | ACA | CAT | TAC | CAC | GAA | ATG | 864 |
| Arg | His | Ser 275 | Ser | Thr | Gln | Leu | Trp 280 | Leu | Ile | Thr | His | Tyr 285 | His | Glu | Met | |
| GGA | TCG | TTG | TAT | GAC | TAC | CTT | CAG | CTC | ACC | ACT | CTG | GAC | ACG | GTT | AGC | 912 |
| Gly | Ser | Leu | Tyr 290 | Asp | Tyr | Leu | Gln | Leu 295 | Thr | Thr | Leu | Asp | Thr 300 | Val | Ser | |
| TGC | CTT | CGG | ATC | GTG | TTG | TCC | ATA | GCC | AGC | GGC | CTT | GCA | CAC | TTG | CAC | 960 |
| Cys 305 | Leu | Arg | Ile | Val | Leu 310 | Ser | Ile | Ala | Ser | Gly 315 | Leu | Ala | His | Leu | His 320 | |
| ATA | GAG | ATA | TTT | GGG | ACC | CAG | GGG | AAG | TCT | GCC | ATC | GCC | CAC | CGA | GAT | 1008 |
| Ile | Glu | Ile | Phe | Gly 325 | Thr | Gln | Gly | Lys | Ser 330 | Ala | Ile | Ala | His | Arg 335 | Asp | |
| CTA | AAG | AGC | AAA | AAC | ATC | CTC | GTG | AAG | AAG | AAC | GGA | CAG | TGC | TGC | ATA | 1056 |
| Leu | Lys | Ser | Lys 340 | Asn | Ile | Leu | Val | Lys 345 | Lys | Asn | Gly | Gln | Cys 350 | Cys | Ile | |
| GCA | GAT | TTG | GGC | CTG | GCA | GTC | ATG | CAT | TCC | CAG | AGC | ACG | AAT | CAG | CTT | 1104 |
| Ala | Asp | Leu 355 | Gly | Leu | Ala | Val | Met 360 | His | Ser | Gln | Ser | Thr 365 | Asn | Gln | Leu | |
| GAT | GTG | GGA | AAC | AAC | CCC | CGT | GTG | GGG | ACC | AAG | CGC | TAC | ATG | GCC | CCT | 1152 |
| Asp | Val | Gly | Asn | Asn 370 | Pro | Arg | Val | Gly | Thr 375 | Lys | Arg | Tyr | Met | Ala 380 | Pro | |
| GAA | GTG | CTT | GAT | GAA | ACC | ATC | CAA | GTG | GAT | TGC | TTT | GAT | TCT | TAT | AAG | 1200 |
| Glu | Val | Leu 385 | Asp | Glu | Thr | Ile | Gln 390 | Val | Asp | Cys | Phe | Asp 395 | Ser | Tyr | Lys 410 | |

| | | | | | | | | | | | | | | | | |
|---|---|---|---|---|---|---|---|---|---|---|---|---|---|---|---|---|
|AGG|GTC|GAT|ATT|TGG|GCC|TTT|GGC|CTC|GTT|CTG|TGG|GAA|GTG|GCC|AGG|1248|
|Arg|Val|Asp|Ile|Trp|Ala|Phe|Gly|Leu|Val|Leu|Trp|Glu|Val|Ala|Arg| |
| | | |415| | | | |420| | | | |425| | | |

```
    AGG  ATG  GTG  AGC  AAT  GGT  ATA  GTG  GAA  GAT  TAC  AAG  CCA  CCA  TTC  TAT           1296
    Arg  Met  Val  Ser  Asn  Gly  Ile  Val  Glu  Asp  Tyr  Lys  Pro  Pro  Phe  Tyr
                   430                     435                     440

GAT  GTT  GTT  CCC  AAT  GAC  CCA  AGT  TTT  GAA  GAT  ATG  AGG  AAA  GTT  GTC               1344
Asp  Val  Val  Pro  Asn  Asp  Pro  Ser  Phe  Glu  Asp  Met  Arg  Lys  Val  Val
               445                     450                     455

TGT  GTG  GAT  CAA  CAG  AGG  CCA  AAC  ATA  CCT  AAC  AGA  TGG  TTC  TCA  GAC               1392
Cys  Val  Asp  Gln  Gln  Arg  Pro  Asn  Ile  Pro  Asn  Arg  Trp  Phe  Ser  Asp
     460                     465                     470

CCG  ACA  TTA  ACT  TCT  CTG  GCG  AAC  GTG  ATG  AAA  GAA  TGC  TGG  TAC  CAG               1440
Pro  Thr  Leu  Thr  Ser  Leu  Ala  Asn  Val  Met  Lys  Glu  Cys  Trp  Tyr  Gln
475                      480                     485                     490

AAC  CCA  TCC  GCC  AGA  CTC  ACA  GCT  CTA  CGT  ATC  AAA  AAG  ACT  TTG  ACC               1488
Asn  Pro  Ser  Ala  Arg  Leu  Thr  Ala  Leu  Arg  Ile  Lys  Lys  Thr  Leu  Thr
                    495                     500                     505

AAA  ATT  GAT  AAC  TCC  CTA  GAC  AAA  TTA  AAA  ACT  GAC  TGT  TGA                         1530
Lys  Ile  Asp  Asn  Ser  Leu  Asp  Lys  Leu  Lys  Thr  Asp  Cys
               510                     515
```

( 2 ) INFORMATION FOR SEQ ID NO: 2:

( i ) SEQUENCE CHARACTERISTICS:
        ( A ) LENGTH: 1506
        ( B ) TYPE: nucleic acid
        ( C ) STRANDEDNESS: double
        ( D ) TOPOLOGY: linear ( x i ) SEQUENCE DESCRIPTION: SEQ ID NO: 2:

```
ATG  GCG  GAG  TCG  GCC  GGA  GCC  TCC  TCC  TTC  TTC  CCC  CTT  GTT  GTC  CTC                48
Met  Ala  Glu  Ser  Ala  Gly  Ala  Ser  Ser  Phe  Phe  Pro  Leu  Val  Val  Leu
 1                    5                     10                      15

CTG  CTC  GCC  GGC  AGT  GGC  GGG  TCC  GGG  CCC  CGG  GGG  ATC  CAG  GCT  CTG                96
Leu  Leu  Ala  Gly  Ser  Gly  Gly  Ser  Gly  Pro  Arg  Gly  Ile  Gln  Ala  Leu
               20                      25                     30

CTG  TGT  GCA  TGC  ACC  AGC  TGC  CTA  CAG  ACC  AAC  TAC  ACC  TGC  GAA  ACA                144
Leu  Cys  Ala  Cys  Thr  Ser  Cys  Leu  Gln  Thr  Asn  Tyr  Thr  Cys  Glu  Thr
          35                      40                      45

GAT  GGG  GCC  TGC  ATG  GTC  TCC  ATC  TTT  AAC  CTG  GAT  GGC  ATG  GAG  CAC                192
Asp  Gly  Ala  Cys  Met  Val  Ser  Ile  Phe  Asn  Leu  Asp  Gly  Met  Glu  His
     50                      55                     60

CAC  GTA  CGC  ACC  TGC  ATC  CCC  AAG  GTG  GAG  CTT  GTG  CCT  GCT  GGG  AAG                240
His  Val  Arg  Thr  Cys  Ile  Pro  Lys  Val  Glu  Leu  Val  Pro  Ala  Gly  Lys
65                      70                      75                      80

CCC  TTC  TAC  TGC  CTG  AGT  TCA  GAG  GAC  CTG  CGC  AAC  ACG  CAC  TGC  TGC                288
Pro  Phe  Tyr  Cys  Leu  Ser  Ser  Glu  Asp  Leu  Arg  Asn  Thr  His  Cys  Cys
                    85                      90                     95

TAT  ATT  GAC  TTC  TGC  AAC  AAG  ATT  GAC  CTG  AGG  GTG  CCC  AGT  GGA  CAC                336
Tyr  Ile  Asp  Phe  Cys  Asn  Lys  Ile  Asp  Leu  Arg  Val  Pro  Ser  Gly  His
               100                     105                     110

CTC  AAG  GAG  CCT  GAG  CAC  CCC  TCC  ATG  TGG  GGC  CCT  GTG  GAG  CTG  GTC                384
Leu  Lys  Glu  Pro  Glu  His  Pro  Ser  Met  Trp  Gly  Pro  Val  Glu  Leu  Val
          115                     120                     125

GGC  ATC  ATT  GCC  GGT  CCT  GTC  TTC  CTC  CTC  TTC  CTC  ATC  ATC  ATC  ATC                432
Gly  Ile  Ile  Ala  Gly  Pro  Val  Phe  Leu  Leu  Phe  Leu  Ile  Ile  Ile  Ile
     130                     135                     140

GTC  TTC  CTG  GTC  ATC  AAC  TAT  CAT  CAG  CGT  GTC  TAC  CAC  AAC  CGC  CAA                480
Val  Phe  Leu  Val  Ile  Asn  Tyr  His  Gln  Arg  Val  Tyr  His  Asn  Arg  Gln
145                     150                     155                     160

AGA  CTG  GAC  ATG  GAG  GAC  CCC  TCA  TGT  GAG  ATG  TGT  CTC  TCC  AAA  GAC                528
```

| | | | | | | | | | | | | | | | | |
|---|---|---|---|---|---|---|---|---|---|---|---|---|---|---|---|---|
| Arg | Leu | Asp | Met | Glu 165 | Asp | Pro | Ser | Cys | Glu 170 | Met | Cys | Leu | Ser | Lys 175 | Asp | |
| AAG | ACG | CTC | CAG | GAT | CTC | GTC | TAC | GAT | CTC | TCC | ACT | TCA | GGA | TCG | GGC | 576 |
| Lys | Thr | Leu | Gln 180 | Asp | Leu | Val | Tyr | Asp 185 | Leu | Ser | Thr | Ser | Gly 190 | Ser | Gly | |
| TCA | GGG | TTA | CCC | CTT | TTT | GTC | CAG | CGC | ACA | GTG | GCC | CGA | ACC | ATT | GTT | 624 |
| Ser | Gly | Leu 195 | Pro | Leu | Phe | Val | Gln 200 | Arg | Thr | Val | Ala | Arg 205 | Thr | Ile | Val | |
| TTA | CAA | GAG | ATT | ATC | GGC | AAG | GGC | CGG | TTT | GGG | GAA | GTA | TGG | CGT | GGC | 672 |
| Leu | Gln 210 | Glu | Ile | Ile | Gly | Lys 215 | Gly | Arg | Phe | Gly | Glu 220 | Val | Trp | Arg | Gly | |
| CGC | TGG | AGG | GGT | GGT | GAT | GTG | GCT | GTG | AAA | ATC | TTC | TCT | TCC | CGT | GAA | 720 |
| Arg 225 | Trp | Arg | Gly | Gly | Asp 230 | Val | Ala | Val | Lys | Ile 235 | Phe | Ser | Ser | Arg | Glu 240 | |
| GAG | CGG | TCG | TGG | TTC | CGG | GAG | GCA | GAG | ATC | TAC | CAG | ACT | GTC | ATG | CTG | 768 |
| Glu | Arg | Ser | Trp | Phe 245 | Arg | Glu | Ala | Glu | Ile 250 | Tyr | Gln | Thr | Val | Met 255 | Leu | |
| CGC | CAT | GAA | AAC | ATC | CTT | GGG | TTT | ATT | GCT | GCT | GAC | AAT | AAA | GAC | AAT | 816 |
| Arg | His | Glu | Asn 260 | Ile | Leu | Gly | Phe | Ile 265 | Ala | Ala | Asp | Asn | Lys 270 | Asp | Asn | |
| GGC | ACC | TGG | ACC | CAG | CTG | TGG | CTT | GTC | TCT | GAC | TAT | CAC | GAG | CAC | GGC | 864 |
| Gly | Thr | Trp 275 | Thr | Gln | Leu | Trp | Leu 280 | Val | Ser | Asp | Tyr | His 285 | Glu | His | Gly | |
| TCA | CTG | TTC | GAT | TAT | CTG | AAC | CGC | TAC | ACA | GTG | ACC | ATT | GAG | GGG | ATG | 912 |
| Ser | Leu | Phe 290 | Asp | Tyr | Leu | Asn | Arg 295 | Tyr | Thr | Val | Thr | Ile 300 | Glu | Gly | Met | |
| ATT | AAA | CTG | GCC | CTG | TCT | GCA | GCC | AGT | GGT | TTG | GCA | CAC | CTG | CAT | ATG | 960 |
| Ile | Lys | Leu | Ala | Leu | Ser 310 | Ala | Ala | Ser | Gly | Leu 315 | Ala | His | Leu | His | Met 320 | |
| 305 | | | | | | | | | | | | | | | | |
| GAG | ATT | GTG | GGC | ACT | CAG | GGG | AAG | CCT | GGA | ATT | GCT | CAT | CGA | GAC | TTG | 1008 |
| Glu | Ile | Val | Gly | Thr 325 | Gln | Gly | Lys | Pro | Gly 330 | Ile | Ala | His | Arg | Asp 335 | Leu | |
| AAG | TCA | AAG | AAC | ATT | CTG | GTG | AAG | AAG | AAT | GGC | ATG | TGT | GCC | ATT | GCA | 1056 |
| Lys | Ser | Lys | Asn 340 | Ile | Leu | Val | Lys | Lys 345 | Asn | Gly | Met | Cys | Ala 350 | Ile | Ala | |
| GAC | CTG | GGC | CTA | GCT | GTC | CGT | CAC | GAT | GCT | GTC | ACT | GAC | ACC | ATA | GAC | 1104 |
| Asp | Leu | Gly 355 | Leu | Ala | Val | Arg | His 360 | Asp | Ala | Val | Thr | Asp 365 | Thr | Ile | Asp | |
| ATT | GCT | CCA | AAT | CAG | AGG | GTG | GGA | ACC | AAA | CGA | TAC | ATG | GCT | CCT | GAA | 1152 |
| Ile | Ala | Pro | Asn | Gln 370 | Arg | Val | Gly | Thr | Lys 375 | Arg | Tyr | Met | Ala | Pro 380 | Glu | |
| GTA | CTT | GAC | GAG | ACC | ATC | AAC | ATG | AAG | CAC | TTT | GAC | TCC | TTC | AAG | TGT | 1200 |
| Val 385 | Leu | Asp | Glu | Thr | Ile 390 | Asn | Met | Lys | His | Phe 395 | Asp | Ser | Phe | Lys | Cys 400 | |
| GCC | GAT | ATC | TAC | GCC | CTC | GGG | CTT | GTC | TAT | TGG | GAG | ATT | GCT | CGG | AGG | 1248 |
| Ala | Asp | Ile | Tyr | Ala 405 | Leu | Gly | Leu | Val | Tyr 410 | Trp | Glu | Ile | Ala | Arg 415 | Arg | |
| TGC | AAT | TCT | GGA | GGA | GTC | CAT | GAA | GAG | TAT | CAA | CTG | CCA | TAT | TAT | GAT | 1296 |
| Cys | Asn | Ser | Gly 420 | Gly | Val | His | Glu | Glu 425 | Tyr | Gln | Leu | Pro | Tyr 430 | Tyr | Asp | |
| TTA | GTG | CCC | TCT | GAC | CCT | TCC | ATT | GAG | GAA | ATG | CGA | AAG | GTC | GTC | TGT | 1344 |
| Leu | Val | Pro 435 | Ser | Asp | Pro | Ser | Ile 440 | Glu | Glu | Met | Arg | Lys 445 | Val | Val | Cys | |
| GAC | CAG | AAG | CTA | CGG | CCC | AAT | GTC | CCC | AAC | TGG | TGG | CAG | AGT | TAT | GAG | 1392 |
| Asp | Gln | Lys 450 | Leu | Arg | Pro | Asn | Val 455 | Pro | Asn | Trp | Trp | Gln 460 | Ser | Tyr | Glu | |
| GCC | TTG | CGA | GTG | ATG | GGG | AAG | ATG | ATG | CGG | GAG | TGC | TGG | TAC | GCC | AAT | 1440 |
| Ala | Leu | Arg | Val | Met 470 | Gly | Lys | Met | Met | Arg 475 | Glu | Cys | Trp | Tyr | Ala | Asn 480 | |
| 465 | | | | | | | | | | | | | | | | |
| GGT | GCT | GCC | CGC | CTG | ACA | GCG | CTG | CGC | ATC | AAG | AAG | ACT | TTG | TCC | CAG | 1488 |

|   |   |   |   |   |   |   |   |   |   |   |   |   |   |   |   |
|---|---|---|---|---|---|---|---|---|---|---|---|---|---|---|---|
| Gly | Ala | Ala | Arg | Leu | Thr | Ala | Leu | Arg | Ile | Lys | Lys | Thr | Leu | Ser | Gln |
|   |   |   |   | 485 |   |   |   | 490 |   |   |   | 495 |   |   |   |

```
GAA GAC GTG AAG ATT TAA                                                      1506
Glu Asp Val Lys Ile
            500
```

(2) INFORMATION FOR SEQ ID NO: 3:

(i) SEQUENCE CHARACTERISTICS:
(A) LENGTH: 1518
(B) TYPE: nucleic acid
(C) STRANDEDNESS: double
(D) TOPOLOGY: linear (xi) SEQUENCE DESCRIPTION: SEQ ID NO: 3:

```
ATG ACC CTG GGG ATT TTT CGA AGG GTC TTT TTG ATG CTG TCG GTG GCC              48
Met Thr Leu Gly Ile Phe Arg Arg Val Phe Leu Met Leu Ser Val Ala
 1               5                  10                  15

TTG GGC CTA ACT AAG GGA GAC TTG GTG AAG CCC TCC AGG GGT CAG CTG              96
Leu Gly Leu Thr Lys Gly Asp Leu Val Lys Pro Ser Arg Gly Gln Leu
                20                  25                  30

GTA AAC TGC ACT TGT GAG AAC CCA CAC TGC AAG AGG CCA ATC TGC CAG             144
Val Asn Cys Thr Cys Glu Asn Pro His Cys Lys Arg Pro Ile Cys Gln
            35                  40                  45

GGG GCA TGG TGC ACA GTG GTG CTA GTT CGA GAG CAG GGC AGG CAC CCC             192
Gly Ala Trp Cys Thr Val Val Leu Val Arg Glu Gln Gly Arg His Pro
 50                  55                  60

CAG GTC TAT CGG GGC TGC GGG AGC CTG AAC CAG GAG CTC TGC CTG GGA             240
Gln Val Tyr Arg Gly Cys Gly Ser Leu Asn Gln Glu Leu Cys Leu Gly
 65                  70                  75                  80

CGT CCC ACG GAG TTT GTG AAC CAT CAC TGC TGC TAT AGA TCC TTC TGC             288
Arg Pro Thr Glu Phe Val Asn His His Cys Cys Tyr Arg Ser Phe Cys
                 85                  90                  95

AAC CAC AAT GTG TCC CTG ATG CTG GAG GCC ACC CAA ACT CCT TCG GAG             336
Asn His Asn Val Ser Leu Met Leu Glu Ala Thr Gln Thr Pro Ser Glu
            100                 105                 110

GAG CCA GAA GTA GAT GCC CAT CTG CCT CTG ATC CTG GGT CCC GTG CTG             384
Glu Pro Glu Val Asp Ala His Leu Pro Leu Ile Leu Gly Pro Val Leu
        115                 120                 125

GCC TTG CTG GTC CTG GTG GCC CTG GGC ACT CTG GGC TTG TGG CGT GTC             432
Ala Leu Leu Val Leu Val Ala Leu Gly Thr Leu Gly Leu Trp Arg Val
130                 135                 140

CGG AGA AGG CAG GAG AAG CAG CGG GGT CTG CAC AGT GAC CTG GGC GAG             480
Arg Arg Arg Gln Glu Lys Gln Arg Gly Leu His Ser Asp Leu Gly Glu
145                 150                 155                 160

TCC AGT CTC ATC CTG AAG GCA TCG GAA CAG GGA GAC AGC ATG TTG GGG             528
Ser Ser Leu Ile Leu Lys Ala Ser Glu Gln Gly Asp Ser Met Leu Gly
                165                 170                 175

GAC TTC CTG GTC AGC GAC TGT ACC ACA GGC AGC GGC TCA GGG CTA CCC             576
Asp Phe Leu Val Ser Asp Cys Thr Thr Gly Ser Gly Ser Gly Leu Pro
            180                 185                 190

TTC TTG GTG CAG AGG ACA GTA GCG CGA CAG GTT GCA CTG GTG GAG TGT             624
Phe Leu Val Gln Arg Thr Val Ala Arg Gln Val Ala Leu Val Glu Cys
        195                 200                 205

GTG GGA AAG GGC CGA TAT GGC GAG GTG TGG CGC GGT TCG TGG CAT GGC             672
Val Gly Lys Gly Arg Tyr Gly Glu Val Trp Arg Gly Ser Trp His Gly
210                 215                 220

GAG AGT GTG GCG GTC AAG ATT TTC TCC TCA CGA GAT GAG CAG TCC TGG             720
Glu Ser Val Ala Val Lys Ile Phe Ser Ser Arg Asp Glu Gln Ser Trp
225                 230                 235                 240

TTC CGG GAG ACA GAG ATC TAC AAC ACA GTT CTG CTT AGA CAC GAC AAC             768
Phe Arg Glu Thr Glu Ile Tyr Asn Thr Val Leu Leu Arg His Asp Asn
```

-continued

| | | | | | | | | | | | | | | | | |
|---|---|---|---|---|---|---|---|---|---|---|---|---|---|---|---|---|
| | | | 245 | | | | | 250 | | | | | 255 | | | |
| ATC | CTA | GGC | TTC | ATC | GCC | TCC | GAC | ATG | ACC | TCG | CGG | AAC | TCC | AGC | ACG | 816 |
| Ile | Leu | Gly | Phe 260 | Ile | Ala | Ser | Asp | Met 265 | Thr | Ser | Arg | Asn | Ser 270 | Ser | Thr | |
| CAG | CTG | TGG | CTT | ATC | ACC | CAC | TAC | CAC | GAG | CAT | GGC | TCC | CTC | TAT | GAC | 864 |
| Gln | Leu | Trp 275 | Leu | Ile | Thr | His | Tyr 280 | His | Glu | His | Gly | Ser 285 | Leu | Tyr | Asp | |
| TTT | CTG | CAG | AGG | CAG | ACG | CTG | GAG | CCC | CAG | TTG | GCC | CTG | AGG | CTG | GCT | 912 |
| Phe | Leu 290 | Gln | Arg | Gln | Thr | Leu 295 | Glu | Pro | Gln | Leu | Ala 300 | Leu | Arg | Leu | Ala | |
| GTG | TCC | GCG | GCC | TGC | GCT | GGC | CTG | GCG | CAC | CTG | CAT | GTA | GAG | ATC | TTT | 960 |
| Val 305 | Ser | Ala | Ala | Cys | Ala 310 | Gly | Leu | Ala | His | Leu 315 | His | Val | Glu | Ile | Phe 320 | |
| GGC | ACT | CAA | GGC | AAA | CCA | GCC | ATC | GCC | CAT | CGT | GAC | CTC | AAG | AGC | CGC | 1008 |
| Gly | Thr | Gln | Gly | Lys 325 | Pro | Ala | Ile | Ala | His 330 | Arg | Asp | Leu | Lys | Ser 335 | Arg | |
| AAC | GTG | CTG | GTC | AAG | AGC | AAC | TTG | CAG | TGT | TGC | ATT | GCA | GAC | CTG | GGA | 1056 |
| Asn | Val | Leu | Val 340 | Lys | Ser | Asn | Leu | Gln 345 | Cys | Cys | Ile | Ala | Asp 350 | Leu | Gly | |
| TTG | GCT | GTG | ATG | CAC | TCG | CAA | AGC | AGC | GAT | TAC | CTG | GAC | ATT | GGT | AAC | 1104 |
| Leu | Ala | Val | Met 355 | His | Ser | Gln | Ser | Ser 360 | Asp | Tyr | Leu | Asp | Ile 365 | Gly | Asn | |
| AAC | CCC | CGA | GTG | GGT | ACC | AAG | AGA | TAC | ATG | GCA | CCC | GAG | GTG | CTG | GAT | 1152 |
| Asn | Pro 370 | Arg | Val | Gly | Thr | Lys 375 | Arg | Tyr | Met | Ala | Pro 380 | Glu | Val | Leu | Asp | |
| GAG | CAG | ATC | CGC | ACA | GAC | TGT | TTT | GAG | TCG | TAC | AAG | TGG | ACA | GAC | ATC | 1200 |
| Glu 385 | Gln | Ile | Arg | Thr | Asp 390 | Cys | Phe | Glu | Ser | Tyr 395 | Lys | Trp | Thr | Asp | Ile 400 | |
| TGG | GCC | TTC | GGC | TTA | GTG | CTA | TGG | GAG | ATT | GCC | CGG | CGG | ACC | ATC | ATC | 1248 |
| Trp | Ala | Phe | Gly | Leu 405 | Val | Leu | Trp | Glu | Ile 410 | Ala | Arg | Arg | Thr | Ile 415 | Ile | |
| AAT | GGC | ATT | GTG | GAG | GAC | TAC | AGG | CCA | CCC | TTC | TAT | GAC | ATG | GTA | CCC | 1296 |
| Asn | Gly | Ile | Val 420 | Glu | Asp | Tyr | Arg | Pro 425 | Pro | Phe | Tyr | Asp | Met 430 | Val | Pro | |
| AAT | GAC | CCC | AGT | TTT | GAG | GAC | ATG | AAA | AAG | GTG | GTG | TGT | GTT | GAC | CAG | 1344 |
| Asn | Asp | Pro 435 | Ser | Phe | Glu | Asp | Met 440 | Lys | Lys | Val | Val | Cys 445 | Val | Asp | Gln | |
| CAG | ACC | CCC | ACC | ATC | CCT | AAC | CGA | CTG | GCA | GCA | GAT | CCG | GTC | CTC | TCC | 1392 |
| Gln | Thr 450 | Pro | Thr | Ile | Pro | Asn 455 | Arg | Leu | Ala | Ala | Asp 460 | Pro | Val | Leu | Ser | |
| GGG | CTG | GCC | CAG | ATG | ATG | CGA | GAG | TGC | TGG | TAC | CCC | AAC | CCC | TCC | GCT | 1440 |
| Gly | Leu | Ala | Gln | Met 470 | Met | Arg | Glu | Cys | Trp | Tyr 475 | Pro | Asn | Pro | Ser | Ala 480 | |
| | | | | | | | | | | | | | | | | |
| Gly 465 | | | | | | | | | | | | | | | | |
| CGC | CTC | ACC | GCA | CTG | CGC | ATA | AAG | AAG | ACA | TTA | CAG | AAG | CTC | AGC | CAG | 1488 |
| Arg | Leu | Thr | Ala | Leu 485 | Arg | Ile | Lys | Lys | Thr 490 | Leu | Gln | Lys | Leu | Ser 495 | Gln | |
| AAT | CCA | GAG | AAA | CCC | AAA | GTG | ATT | CAC | TAG | | | | | | | 1518 |
| Asn | Pro | Glu | Lys 500 | Pro | Lys | Val | Ile | His 505 | | | | | | | | |

( 2 ) INFORMATION FOR SEQ ID NO: 4:

( i ) SEQUENCE CHARACTERISTICS:
        ( A ) LENGTH: 1506
        ( B ) TYPE: nucleic acid
        ( C ) STRANDEDNESS: double
        ( D ) TOPOLOGY: linear ( x i ) SEQUENCE DESCRIPTION: SEQ ID NO: 4:

| ATG | GAG | GCG | GCG | TCG | GCT | GCT | TTG | CGT | CGC | TGC | CTG | CTT | CTC | ATC | GTG | 48 |
|---|---|---|---|---|---|---|---|---|---|---|---|---|---|---|---|---|
| Met 1 | Glu | Ala | Ala | Ser 5 | Ala | Ala | Leu | Arg | Arg 10 | Cys | Leu | Leu | Leu | Ile 15 | Val | |

| | | | | | | | | | | | | | | | | |
|---|---|---|---|---|---|---|---|---|---|---|---|---|---|---|---|---|
| TTG | GTG | GCG | GCG | GCG | ACG | CTG | CTC | CCG | GGG | GCG | AAG | GCA | TTA | CAG | TGT | 96 |
| Leu | Val | Ala | Ala | Ala | Thr | Leu | Leu | Pro | Gly | Ala | Lys | Ala | Leu | Gln | Cys | |
| | | 20 | | | | | 25 | | | | | 30 | | | | |
| TTC | TGC | CAC | CTC | TGT | ACA | AAG | GAC | AAT | TTT | ACT | TGT | GAG | ACA | GAT | GGT | 144 |
| Phe | Cys | His | Leu | Cys | Thr | Lys | Asp | Asn | Phe | Thr | Cys | Glu | Thr | Asp | Gly | |
| | | 35 | | | | 40 | | | | | 45 | | | | | |
| CTC | TGC | TTT | GTC | TCA | GTC | ACC | GAG | ACC | ACA | GAC | AAA | GTT | ATA | CAC | AAT | 192 |
| Leu | Cys | Phe | Val | Ser | Val | Thr | Glu | Thr | Thr | Asp | Lys | Val | Ile | His | Asn | |
| | 50 | | | | | 55 | | | | | 60 | | | | | |
| AGC | ATG | TGT | ATA | GCT | GAA | ATC | GAC | CTA | ATT | CCC | CGA | GAC | AGG | CCA | TTT | 240 |
| Ser | Met | Cys | Ile | Ala | Glu | Ile | Asp | Leu | Ile | Pro | Arg | Asp | Arg | Pro | Phe | |
| 65 | | | | | 70 | | | | | 75 | | | | | 80 | |
| GTT | TGT | GCA | CCA | TCT | TCA | AAA | ACA | GGG | GCA | GTT | ACG | TAT | TGC | TGC | AAT | 288 |
| Val | Cys | Ala | Pro | Ser | Ser | Lys | Thr | Gly | Ala | Val | Thr | Tyr | Cys | Cys | Asn | |
| | | | | 85 | | | | | 90 | | | | | 95 | | |
| CAG | GAT | CAC | TGC | AAT | AAA | ATA | GAA | CTC | CCA | ACT | ACA | GGA | CCT | TTT | TCA | 336 |
| Gln | Asp | His | Cys | Asn | Lys | Ile | Glu | Leu | Pro | Thr | Thr | Gly | Pro | Phe | Ser | |
| | | | 100 | | | | | 105 | | | | | 110 | | | |
| GAA | AAG | CAG | TCA | GCT | GGC | CTC | GGT | CCT | GTG | GAG | CTG | GCA | GCT | GTC | ATT | 384 |
| Glu | Lys | Gln | Ser | Ala | Gly | Leu | Gly | Pro | Val | Glu | Leu | Ala | Ala | Val | Ile | |
| | | 115 | | | | | 120 | | | | | 125 | | | | |
| GCT | GGT | CCA | GTC | TGC | TTC | GTC | TGC | ATT | GCA | CTT | ATG | CTG | ATG | GTC | TAT | 432 |
| Ala | Gly | Pro | Val | Cys | Phe | Val | Cys | Ile | Ala | Leu | Met | Leu | Met | Val | Tyr | |
| | 130 | | | | | 135 | | | | | 140 | | | | | |
| ATC | TGC | CAT | AAC | CGC | ACT | GTC | ATT | CAC | CAC | CGC | GTG | CCA | AAT | GAA | GAG | 480 |
| Ile | Cys | His | Asn | Arg | Thr | Val | Ile | His | His | Arg | Val | Pro | Asn | Glu | Glu | |
| 145 | | | | | 150 | | | | | 155 | | | | | 160 | |
| GAT | CCC | TCA | CTA | GAT | CGC | CCT | TTC | ATT | TCA | GAG | GGC | ACC | ACC | TTA | AAA | 528 |
| Asp | Pro | Ser | Leu | Asp | Arg | Pro | Phe | Ile | Ser | Glu | Gly | Thr | Thr | Leu | Lys | |
| | | | | 165 | | | | | 170 | | | | | 175 | | |
| GAT | TTA | ATT | TAT | GAT | ATG | ACA | ACA | TCA | GGG | TCT | GGA | TCA | GGT | TTA | CCA | 576 |
| Asp | Leu | Ile | Tyr | Asp | Met | Thr | Thr | Ser | Gly | Ser | Gly | Ser | Gly | Leu | Pro | |
| | | | 180 | | | | | 185 | | | | | 190 | | | |
| CTG | CTT | GTT | CAA | AGA | ACA | ATT | GCA | AGG | ACC | ATT | GTG | CTA | CAA | GAA | AGC | 624 |
| Leu | Leu | Val | Gln | Arg | Thr | Ile | Ala | Arg | Thr | Ile | Val | Leu | Gln | Glu | Ser | |
| | | 195 | | | | | 200 | | | | | 205 | | | | |
| ATC | GGC | AAA | GGT | CGG | TTT | GGA | GAA | GTT | TGG | CGA | GGC | AAA | TGG | CGG | GGA | 672 |
| Ile | Gly | Lys | Gly | Arg | Phe | Gly | Glu | Val | Trp | Arg | Gly | Lys | Trp | Arg | Gly | |
| | 210 | | | | | 215 | | | | | 220 | | | | | |
| GAA | GAA | GTT | GCC | GTG | AAG | ATA | TTC | TCT | TCT | AGA | GAA | GAA | CGT | TCA | TGG | 720 |
| Glu | Glu | Val | Ala | Val | Lys | Ile | Phe | Ser | Ser | Arg | Glu | Glu | Arg | Ser | Trp | |
| 225 | | | | | 230 | | | | | 235 | | | | | 240 | |
| TTC | CGA | GAG | GCA | GAG | ATT | TAT | CAG | ACT | GTA | ATG | TTA | CGC | CAT | GAA | AAT | 768 |
| Phe | Arg | Glu | Ala | Glu | Ile | Tyr | Gln | Thr | Val | Met | Leu | Arg | His | Glu | Asn | |
| | | | | 245 | | | | | 250 | | | | | 255 | | |
| ATC | CTG | GGG | TTT | ATA | GCA | GCA | GAC | AAC | AAA | GAC | AAT | GGT | ACA | TGG | ACT | 816 |
| Ile | Leu | Gly | Phe | Ile | Ala | Ala | Asp | Asn | Lys | Asp | Asn | Gly | Thr | Trp | Thr | |
| | | | 260 | | | | | 265 | | | | | 270 | | | |
| CAG | CTG | TGG | TTG | GTG | TCG | GAT | TAT | CAT | GAG | CAT | GGA | TCC | CTT | TTC | GAT | 864 |
| Gln | Leu | Trp | Leu | Val | Ser | Asp | Tyr | His | Glu | His | Gly | Ser | Leu | Phe | Asp | |
| | | 275 | | | | | 280 | | | | | 285 | | | | |
| TAC | TTG | AAT | AGA | TAC | ACT | GTT | ACT | GTG | GAA | GGA | ATG | ATC | AAA | CTC | GCT | 912 |
| Tyr | Leu | Asn | Arg | Tyr | Thr | Val | Thr | Val | Glu | Gly | Met | Ile | Lys | Leu | Ala | |
| | | 290 | | | | | 295 | | | | | 300 | | | | |
| CTG | TCC | ACG | GCA | AGT | GGT | CTT | GCC | CAT | CTT | CAC | ATG | GAG | ATT | GTT | GGT | 960 |
| Leu | Ser | Thr | Ala | Ser | Gly | Leu | Ala | His | Leu | His | Met | Glu | Ile | Val | Gly | |
| 305 | | | | 310 | | | | | 315 | | | | | | 320 | |
| ACC | CAA | GGA | AAA | CCA | GCT | ATT | GCC | CAT | AGA | GAT | TTG | AAA | TCA | AAG | AAT | 1008 |
| Thr | Gln | Gly | Lys | Pro | Ala | Ile | Ala | His | Arg | Asp | Leu | Lys | Ser | Lys | Asn | |
| | | | | 325 | | | | | 330 | | | | | 335 | | |

| | | | | | | | | | | | | | | | | |
|---|---|---|---|---|---|---|---|---|---|---|---|---|---|---|---|---|
| ATC | TTG | GTG | AAG | AAA | AAT | GGA | ACC | TGT | TGT | ATT | GCA | GAT | TTG | GGA | CTT | 1056 |
| Ile | Leu | Val | Lys<br>340 | Lys | Asn | Gly | Thr | Cys<br>345 | Cys | Ile | Ala | Asp | Leu<br>350 | Gly | Leu | |
| GCT | GTG | AGA | CAT | GAT | TCT | GCC | ACA | GAT | ACA | ATT | GAT | ATT | GCT | CCA | AAC | 1104 |
| Ala | Val | Arg<br>355 | His | Asp | Ser | Ala | Thr<br>360 | Asp | Thr | Ile | Asp | Ile<br>365 | Ala | Pro | Asn | |
| CAC | AGA | GTA | GGC | ACT | AAA | AGG | TAT | ATG | GCC | CCT | GAA | GTT | CTA | GAT | GAT | 1152 |
| His | Arg<br>370 | Val | Gly | Thr | Lys | Arg<br>375 | Tyr | Met | Ala | Pro | Glu<br>380 | Val | Leu | Asp | Asp | |
| TCC | ATA | AAT | ATG | AAA | CAT | TTT | GAA | TCC | TTC | AAA | CGT | GCT | GAC | ATC | TAT | 1200 |
| Ser<br>385 | Ile | Asn | Met | Lys | His<br>390 | Phe | Glu | Ser | Phe | Lys<br>395 | Arg | Ala | Asp | Ile | Tyr<br>400 | |
| GCA | ATG | GGC | TTA | GTA | TTC | TGG | GAA | ATC | GCT | CGA | CGC | TGT | TCC | ATT | GGC | 1248 |
| Ala | Met | Gly | Leu | Val<br>405 | Phe | Trp | Glu | Ile | Ala<br>410 | Arg | Arg | Cys | Ser | Ile<br>415 | Gly | |
| GGA | ATC | CAC | GAA | GAC | TAC | CAG | TTG | CCT | TAC | TAT | GAT | CTT | GTA | CCT | TCT | 1296 |
| Gly | Ile | His | Glu<br>420 | Asp | Tyr | Gln | Leu | Pro<br>425 | Tyr | Tyr | Asp | Leu | Val<br>430 | Pro | Ser | |
| GAT | CCA | TCC | GTT | GAA | GAA | ATG | AGA | AAA | GTA | GTT | TGT | GAA | CAG | AAG | TTA | 1344 |
| Asp | Pro | Ser<br>435 | Val | Glu | Glu | Met | Arg<br>440 | Lys | Val | Val | Cys | Glu<br>445 | Gln | Lys | Leu | |
| AGG | CCA | AAT | ATT | CCC | AAC | AGA | TGG | CAG | AGC | TGT | GAG | GCC | TTG | AGA | GTG | 1392 |
| Arg | Pro<br>450 | Asn | Ile | Pro | Asn | Arg<br>455 | Trp | Gln | Ser | Cys | Glu<br>460 | Ala | Leu | Arg | Val | |
| ATG | GCC | AAA | ATT | ATG | AGA | GAA | TGT | TGG | TAT | GCC | AAT | GGA | GCA | GCT | AGG | 1440 |
| Met<br>465 | Ala | Lys | Ile | Met | Arg<br>470 | Glu | Cys | Trp | Tyr | Ala<br>475 | Asn | Gly | Ala | Ala | Arg<br>480 | |
| CTG | ACA | GCT | TTG | CGA | ATT | AAA | AAA | ACA | TTG | TCA | CAG | CTC | AGC | CAA | CAG | 1488 |
| Leu | Thr | Ala | Leu | Arg<br>485 | Ile | Lys | Lys | Thr | Leu<br>490 | Ser | Gln | Leu | Ser | Gln<br>495 | Gln | |
| GAA | GGC | ATC | AAA | ATG | TAA | | | | | | | | | | | 1506 |
| Glu | Gly | Ile | Lys<br>500 | Met | | | | | | | | | | | | |

( 2 ) INFORMATION FOR SEQ ID NO: 5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GTCTACCAGA AGGGCTGCTT    20

( 2 ) INFORMATION FOR SEQ ID NO: 6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 6:

CCGGAGCCTC CTCCTTCTTC    20

( 2 ) INFORMATION FOR SEQ ID NO: 7:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 7:

TCCCTACTGG GTTTGAGACA        20

( 2 ) INFORMATION FOR SEQ ID NO: 8:

( i ) SEQUENCE CHARACTERISTICS:
           ( A ) LENGTH: 20
           ( B ) TYPE: nucleic acid
           ( C ) STRANDEDNESS: single
           ( D ) TOPOLOGY: linear ( x i ) SEQUENCE DESCRIPTION: SEQ ID NO: 8:

GCTGCGGGAG CCTGAACCAG        20

( 2 ) INFORMATION FOR SEQ ID NO: 9:

( i ) SEQUENCE CHARACTERISTICS:
           ( A ) LENGTH: 20
           ( B ) TYPE: nucleic acid
           ( C ) STRANDEDNESS: single
           ( D ) TOPOLOGY: linear ( x i ) SEQUENCE DESCRIPTION: SEQ ID NO: 9:

AAATCCAATG TTTGAATACT        20

( 2 ) INFORMATION FOR SEQ ID NO: 10:

( i ) SEQUENCE CHARACTERISTICS:
           ( A ) LENGTH: 17
           ( B ) TYPE: nucleic acid
           ( C ) STRANDEDNESS: single
           ( D ) TOPOLOGY: linear ( x i ) SEQUENCE DESCRIPTION: SEQ ID NO: 10:

GTGGCCGTSA ARATYTT        17

( 2 ) INFORMATION FOR SEQ ID NO: 11:

( i ) SEQUENCE CHARACTERISTICS:
           ( A ) LENGTH: 18
           ( B ) TYPE: nucleic acid
           ( C ) STRANDEDNESS: single
           ( D ) TOPOLOGY: linear ( x i ) SEQUENCE DESCRIPTION: SEQ ID NO: 11:

GACYTCTGGR GCCATRTA        18

( 2 ) INFORMATION FOR SEQ ID NO: 12:

( i ) SEQUENCE CHARACTERISTICS:
           ( A ) LENGTH: 21
           ( B ) TYPE: amino acid
           ( C ) STRANDEDNESS:
           ( D ) TOPOLOGY: linear ( x i ) SEQUENCE DESCRIPTION: SEQ ID NO: 12:

Gly Lys Gly Arg Tyr Gly Glu Val Xaa Xaa Xaa Xaa Xaa Xaa Xaa Xaa
 1                 5                        10                   15

Xaa Xaa Xaa Xaa Lys
          20

( 2 ) INFORMATION FOR SEQ ID NO: 13:

( i ) SEQUENCE CHARACTERISTICS:
           ( A ) LENGTH: 21
           ( B ) TYPE: amino acid
           ( C ) STRANDEDNESS:

-continued ( D ) TOPOLOGY: linear ( x i ) SEQUENCE DESCRIPTION: SEQ ID NO: 13:

| Gly | Lys | Gly | Arg | Phe | Gly | Glu | Val | Xaa | Xaa | Xaa | Xaa | Xaa | Xaa | Xaa |
|---|---|---|---|---|---|---|---|---|---|---|---|---|---|---|
| 1 | | | | 5 | | | | | 10 | | | | | 15 |

| Xaa | Xaa | Xaa | Xaa | Lys |
|---|---|---|---|---|
| | | | | 20 |

( 2 ) INFORMATION FOR SEQ ID NO: 14:

( i ) SEQUENCE CHARACTERISTICS:
( A ) LENGTH: 509
( B ) TYPE: amino acid
( C ) STRANDEDNESS:
( D ) TOPOLOGY: linear ( x i ) SEQUENCE DESCRIPTION: SEQ ID NO: 14:

| Met | Val | Asp | Gly | Ala | Met | Ile | Leu | Ser | Val | Leu | Met | Met | Met | Ala | Leu |
|---|---|---|---|---|---|---|---|---|---|---|---|---|---|---|---|
| 1 | | | | 5 | | | | | 10 | | | | | 15 | |

| Pro | Ser | Pro | Ser | Met | Glu | Asp | Glu | Glu | Pro | Lys | Val | Asn | Pro | Lys | Leu |
|---|---|---|---|---|---|---|---|---|---|---|---|---|---|---|---|
| | | | 20 | | | | | 25 | | | | | 30 | | |

| Tyr | Met | Cys | Val | Cys | Glu | Gly | Leu | Ser | Cys | Gly | Asn | Glu | Asp | His | Cys |
|---|---|---|---|---|---|---|---|---|---|---|---|---|---|---|---|
| | | 35 | | | | | 40 | | | | | 45 | | | |

| Glu | Gly | Gln | Gln | Cys | Phe | Ser | Ser | Leu | Ser | Val | Asn | Asp | Gly | Phe | Arg |
|---|---|---|---|---|---|---|---|---|---|---|---|---|---|---|---|
| | 50 | | | | | 55 | | | | | 60 | | | | |

| Val | Tyr | Gln | Lys | Gly | Cys | Phe | Gln | Val | Tyr | Glu | Gln | Gly | Lys | Met | Thr |
|---|---|---|---|---|---|---|---|---|---|---|---|---|---|---|---|
| 65 | | | | | 70 | | | | | 75 | | | | | 80 |

| Cys | Lys | Thr | Pro | Pro | Ser | Pro | Gly | Gln | Ala | Val | Glu | Cys | Cys | Gln | Gly |
|---|---|---|---|---|---|---|---|---|---|---|---|---|---|---|---|
| | | | | 85 | | | | | 90 | | | | | 95 | |

| Asp | Trp | Cys | Asn | Arg | Asn | Val | Thr | Ala | Arg | Leu | Pro | Thr | Lys | Gly | Lys |
|---|---|---|---|---|---|---|---|---|---|---|---|---|---|---|---|
| | | | 100 | | | | | 105 | | | | | 110 | | |

| Ser | Phe | Pro | Gly | Ser | Gln | Asn | Phe | His | Leu | Glu | Val | Gly | Leu | Ile | Ile |
|---|---|---|---|---|---|---|---|---|---|---|---|---|---|---|---|
| | | 115 | | | | | 120 | | | | | 125 | | | |

| Leu | Ser | Val | Val | Phe | Ala | Val | Cys | Leu | Phe | Ala | Cys | Ile | Leu | Gly | Val |
|---|---|---|---|---|---|---|---|---|---|---|---|---|---|---|---|
| | 130 | | | | | 135 | | | | | 140 | | | | |

| Ala | Leu | Arg | Lys | Phe | Lys | Arg | Arg | Asn | Gln | Glu | Arg | Leu | Asn | Pro | Arg |
|---|---|---|---|---|---|---|---|---|---|---|---|---|---|---|---|
| 145 | | | | | 150 | | | | | 155 | | | | | 160 |

| Asp | Val | Glu | Tyr | Gly | Thr | Ile | Glu | Gly | Leu | Ile | Thr | Thr | Asn | Val | Gly |
|---|---|---|---|---|---|---|---|---|---|---|---|---|---|---|---|
| | | | | 165 | | | | | 170 | | | | | 175 | |

| Asp | Ser | Thr | Leu | Ala | Glu | Leu | Leu | Asp | His | Ser | Cys | Thr | Ser | Gly | Ser |
|---|---|---|---|---|---|---|---|---|---|---|---|---|---|---|---|
| | | | 180 | | | | | 185 | | | | | 190 | | |

| Gly | Ser | Gly | Leu | Pro | Phe | Leu | Val | Gln | Arg | Thr | Val | Ala | Arg | Gln | Ile |
|---|---|---|---|---|---|---|---|---|---|---|---|---|---|---|---|
| | | 195 | | | | | 200 | | | | | 205 | | | |

| Thr | Leu | Leu | Glu | Cys | Val | Gly | Lys | Gly | Arg | Tyr | Gly | Glu | Val | Trp | Arg |
|---|---|---|---|---|---|---|---|---|---|---|---|---|---|---|---|
| | 210 | | | | | 215 | | | | | 220 | | | | |

| Gly | Ser | Trp | Gln | Gly | Glu | Asn | Val | Ala | Val | Lys | Ile | Phe | Ser | Ser | Arg |
|---|---|---|---|---|---|---|---|---|---|---|---|---|---|---|---|
| 225 | | | | | 230 | | | | | 235 | | | | | 240 |

| Asp | Glu | Lys | Ser | Trp | Phe | Arg | Glu | Thr | Glu | Leu | Tyr | Asn | Thr | Val | Met |
|---|---|---|---|---|---|---|---|---|---|---|---|---|---|---|---|
| | | | | 245 | | | | | 250 | | | | | 255 | |

| Leu | Arg | His | Glu | Asn | Ile | Leu | Gly | Phe | Ile | Ala | Ser | Asp | Met | Thr | Ser |
|---|---|---|---|---|---|---|---|---|---|---|---|---|---|---|---|
| | | | 260 | | | | | 265 | | | | | 270 | | |

| Arg | His | Ser | Ser | Thr | Gln | Leu | Trp | Leu | Ile | Thr | His | Tyr | His | Glu | Met |
|---|---|---|---|---|---|---|---|---|---|---|---|---|---|---|---|
| | | 275 | | | | | 280 | | | | | 285 | | | |

| Gly | Ser | Leu | Tyr | Asp | Tyr | Leu | Gln | Leu | Thr | Thr | Leu | Asp | Thr | Val | Ser |
|---|---|---|---|---|---|---|---|---|---|---|---|---|---|---|---|
| | 290 | | | | | 295 | | | | | 300 | | | | |

| Cys | Leu | Arg | Ile | Val | Leu | Ser | Ile | Ala | Ser | Gly | Leu | Ala | His | Leu | His |
|---|---|---|---|---|---|---|---|---|---|---|---|---|---|---|---|
| 305 | | | | | 310 | | | | | 315 | | | | | 320 |

```
Ile  Glu  Ile  Phe  Gly  Thr  Gln  Gly  Lys  Ser  Ala  Ile  Ala  His  Arg  Asp
               325                 330                           335

Leu  Lys  Ser  Lys  Asn  Ile  Leu  Val  Lys  Lys  Asn  Gly  Gln  Cys  Cys  Ile
               340                 345                           350

Ala  Asp  Leu  Gly  Leu  Ala  Val  Met  His  Ser  Gln  Ser  Thr  Asn  Gln  Leu
               355                 360                           365

Asp  Val  Gly  Asn  Asn  Pro  Arg  Val  Gly  Thr  Lys  Arg  Tyr  Met  Ala  Pro
     370                      375                 380

Glu  Val  Leu  Asp  Glu  Thr  Ile  Gln  Val  Asp  Cys  Phe  Asp  Ser  Tyr  Lys
385                      390                 395                           400

Arg  Val  Asp  Ile  Trp  Ala  Phe  Gly  Leu  Val  Leu  Trp  Glu  Val  Ala  Arg
               405                 410                           415

Arg  Met  Val  Ser  Asn  Gly  Ile  Val  Glu  Asp  Tyr  Lys  Pro  Pro  Phe  Tyr
               420                 425                           430

Asp  Val  Val  Pro  Asn  Asp  Pro  Ser  Phe  Glu  Asp  Met  Arg  Lys  Val  Val
               435                 440                           445

Cys  Val  Asp  Gln  Gln  Arg  Pro  Asn  Ile  Pro  Asn  Arg  Trp  Phe  Ser  Asp
     450                      455                 460

Pro  Thr  Leu  Thr  Ser  Leu  Ala  Asn  Val  Met  Lys  Glu  Cys  Trp  Tyr  Gln
465                      470                 475                           480

Asn  Pro  Ser  Ala  Arg  Leu  Thr  Ala  Leu  Arg  Ile  Lys  Lys  Thr  Leu  Thr
               485                 490                           495

Lys  Ile  Asp  Asn  Ser  Leu  Asp  Lys  Leu  Lys  Thr  Asp  Cys
               500                 505
```

( 2 ) INFORMATION FOR SEQ ID NO: 15:

( i ) SEQUENCE CHARACTERISTICS:
        ( A ) LENGTH: 501
        ( B ) TYPE: amino acid
        ( C ) STRANDEDNESS:
        ( D ) TOPOLOGY: linear ( x i ) SEQUENCE DESCRIPTION: SEQ ID NO: 15:

```
Met  Ala  Glu  Ser  Ala  Gly  Ala  Ser  Ser  Phe  Phe  Pro  Leu  Val  Val  Leu
 1              5                   10                            15

Leu  Leu  Ala  Gly  Ser  Gly  Gly  Ser  Gly  Pro  Arg  Gly  Ile  Gln  Ala  Leu
               20                  25                            30

Leu  Cys  Ala  Cys  Thr  Ser  Cys  Leu  Gln  Thr  Asn  Tyr  Thr  Cys  Glu  Thr
               35                  40                            45

Asp  Gly  Ala  Cys  Met  Val  Ser  Ile  Phe  Asn  Leu  Asp  Gly  Met  Glu  His
     50                       55                  60

His  Val  Arg  Thr  Cys  Ile  Pro  Lys  Val  Glu  Leu  Val  Pro  Ala  Gly  Lys
65                       70                  75                            80

Pro  Phe  Tyr  Cys  Leu  Ser  Ser  Glu  Asp  Leu  Arg  Asn  Thr  His  Cys  Cys
               85                  90                            95

Tyr  Ile  Asp  Phe  Cys  Asn  Lys  Ile  Asp  Leu  Arg  Val  Pro  Ser  Gly  His
              100                 105                           110

Leu  Lys  Glu  Pro  Glu  His  Pro  Ser  Met  Trp  Gly  Pro  Val  Glu  Leu  Val
              115                 120                           125

Gly  Ile  Ile  Ala  Gly  Pro  Val  Phe  Leu  Leu  Phe  Leu  Ile  Ile  Ile  Ile
     130                      135                 140

Val  Phe  Leu  Val  Ile  Asn  Tyr  His  Gln  Arg  Val  Tyr  His  Asn  Arg  Gln
145                      150                 155                           160

Arg  Leu  Asp  Met  Glu  Asp  Pro  Ser  Cys  Glu  Met  Cys  Leu  Ser  Lys  Asp
              165                 170                           175
```

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
            245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
            275                 280                 285

Ser Leu Phe Asp Tyr Leu Asn Arg Tyr Thr Val Thr Ile Glu Gly Met
    290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
            325                 330                 335

Lys Ser Lys Asn Ile Leu Val Lys Lys Asn Gly Met Cys Ala Ile Ala
            340                 345                 350

Asp Leu Gly Leu Ala Val Arg His Asp Ala Val Thr Asp Thr Ile Asp
            355                 360                 365

Ile Ala Pro Asn Gln Arg Val Gly Thr Lys Arg Tyr Met Ala Pro Glu
    370                 375                 380

Val Leu Asp Glu Thr Ile Asn Met Lys His Phe Asp Ser Phe Lys Cys
385                 390                 395                 400

Ala Asp Ile Tyr Ala Leu Gly Leu Val Tyr Trp Glu Ile Ala Arg Arg
            405                 410                 415

Cys Asn Ser Gly Gly Val His Glu Glu Tyr Gln Leu Pro Tyr Tyr Asp
            420                 425                 430

Leu Val Pro Ser Asp Pro Ser Ile Glu Glu Met Arg Lys Val Val Cys
        435                 440                 445

Asp Gln Lys Leu Arg Pro Asn Val Pro Asn Trp Trp Gln Ser Tyr Glu
    450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
            485                 490                 495

Glu Asp Val Lys Ile
            500

( 2 ) INFORMATION FOR SEQ ID NO: 16:

( i ) SEQUENCE CHARACTERISTICS:
    ( A ) LENGTH: 505
    ( B ) TYPE: amino acid
    ( C ) STRANDEDNESS:
    ( D ) TOPOLOGY: linear ( x i ) SEQUENCE DESCRIPTION: SEQ ID NO: 16:

Met Thr Leu Gly Ile Phe Arg Arg Val Phe Leu Met Leu Ser Val Ala
1               5                   10                  15

Leu Gly Leu Thr Lys Gly Asp Leu Val Lys Pro Ser Arg Gly Gln Leu
            20                  25                  30

```
Val  Asn  Cys  Thr  Cys  Glu  Asn  Pro  His  Cys  Lys  Arg  Pro  Ile  Cys  Gln
          35                  40                      45

Gly  Ala  Trp  Cys  Thr  Val  Val  Leu  Val  Arg  Glu  Gln  Gly  Arg  His  Pro
     50                  55                      60

Gln  Val  Tyr  Arg  Gly  Cys  Gly  Ser  Leu  Asn  Gln  Glu  Leu  Cys  Leu  Gly
65                       70                      75                           80

Arg  Pro  Thr  Glu  Phe  Val  Asn  His  His  Cys  Cys  Tyr  Arg  Ser  Phe  Cys
               85                      90                           95

Asn  His  Asn  Val  Ser  Leu  Met  Leu  Glu  Ala  Thr  Gln  Thr  Pro  Ser  Glu
               100                 105                           110

Glu  Pro  Glu  Val  Asp  Ala  His  Leu  Pro  Leu  Ile  Leu  Gly  Pro  Val  Leu
               115                 120                      125

Ala  Leu  Leu  Val  Leu  Val  Ala  Leu  Gly  Thr  Leu  Gly  Leu  Trp  Arg  Val
     130                 135                      140

Arg  Arg  Arg  Gln  Glu  Lys  Gln  Arg  Gly  Leu  His  Ser  Asp  Leu  Gly  Glu
145                      150                      155                         160

Ser  Ser  Leu  Ile  Leu  Lys  Ala  Ser  Glu  Gln  Gly  Asp  Ser  Met  Leu  Gly
               165                 170                           175

Asp  Phe  Leu  Val  Ser  Asp  Cys  Thr  Thr  Gly  Ser  Gly  Ser  Gly  Leu  Pro
               180                 185                      190

Phe  Leu  Val  Gln  Arg  Thr  Val  Ala  Arg  Gln  Val  Ala  Leu  Val  Glu  Cys
          195                      200                      205

Val  Gly  Lys  Gly  Arg  Tyr  Gly  Glu  Val  Trp  Arg  Gly  Ser  Trp  His  Gly
     210                 215                      220

Glu  Ser  Val  Ala  Val  Lys  Ile  Phe  Ser  Ser  Arg  Asp  Glu  Gln  Ser  Trp
225                      230                 235                         240

Phe  Arg  Glu  Thr  Glu  Ile  Tyr  Asn  Thr  Val  Leu  Leu  Arg  His  Asp  Asn
               245                 250                           255

Ile  Leu  Gly  Phe  Ile  Ala  Ser  Asp  Met  Thr  Ser  Arg  Asn  Ser  Ser  Thr
               260                 265                           270

Gln  Leu  Trp  Leu  Ile  Thr  His  Tyr  His  Glu  His  Gly  Ser  Leu  Tyr  Asp
          275                      280                      285

Phe  Leu  Gln  Arg  Gln  Thr  Leu  Glu  Pro  Gln  Leu  Ala  Leu  Arg  Leu  Ala
     290                      295                      300

Val  Ser  Ala  Ala  Cys  Ala  Gly  Leu  Ala  His  Leu  His  Val  Glu  Ile  Phe
305                      310                      315                         320

Gly  Thr  Gln  Gly  Lys  Pro  Ala  Ile  Ala  His  Arg  Asp  Leu  Lys  Ser  Arg
               325                      330                           335

Asn  Val  Leu  Val  Lys  Ser  Asn  Leu  Gln  Cys  Cys  Ile  Ala  Asp  Leu  Gly
               340                 345                           350

Leu  Ala  Val  Met  His  Ser  Gln  Ser  Ser  Asp  Tyr  Leu  Asp  Ile  Gly  Asn
          355                 360                      365

Asn  Pro  Arg  Val  Gly  Thr  Lys  Arg  Tyr  Met  Ala  Pro  Glu  Val  Leu  Asp
     370                 375                      380

Glu  Gln  Ile  Arg  Thr  Asp  Cys  Phe  Glu  Ser  Tyr  Lys  Trp  Thr  Asp  Ile
385                      390                      395                         400

Trp  Ala  Phe  Gly  Leu  Val  Leu  Trp  Glu  Ile  Ala  Arg  Arg  Thr  Ile  Ile
               405                      410                           415

Asn  Gly  Ile  Val  Glu  Asp  Tyr  Arg  Pro  Pro  Phe  Tyr  Asp  Met  Val  Pro
               420                 425                           430

Asn  Asp  Pro  Ser  Phe  Glu  Asp  Met  Lys  Lys  Val  Val  Cys  Val  Asp  Gln
               435                 440                           445

Gln  Thr  Pro  Thr  Ile  Pro  Asn  Arg  Leu  Ala  Ala  Asp  Pro  Val  Leu  Ser
```

|     | 450 |     |     |     | 455 |     |     |     | 460 |     |     |     |     |
|---|---|---|---|---|---|---|---|---|---|---|---|---|---|

Gly Leu Ala Gln Met Met Arg Glu Cys Trp Tyr Pro Asn Pro Ser Ala
465                     470                     475                     480

Arg Leu Thr Ala Leu Arg Ile Lys Lys Thr Leu Gln Lys Leu Ser Gln
                485                     490                     495

Asn Pro Glu Lys Pro Lys Val Ile His
            500             505

( 2 ) INFORMATION FOR SEQ ID NO: 17:

( i ) SEQUENCE CHARACTERISTICS:
       ( A ) LENGTH: 501
       ( B ) TYPE: amino acid
       ( C ) STRANDEDNESS:
       ( D ) TOPOLOGY: linear ( x i ) SEQUENCE DESCRIPTION: SEQ ID NO: 17:

Met Glu Ala Ala Ser Ala Ala Leu Arg Arg Cys Leu Leu Leu Ile Val
1               5                   10                  15

Leu Val Ala Ala Ala Thr Leu Leu Pro Gly Ala Lys Ala Leu Gln Cys
            20                  25                  30

Phe Cys His Leu Cys Thr Lys Asp Asn Phe Thr Cys Glu Thr Asp Gly
        35                  40                  45

Leu Cys Phe Val Ser Val Thr Glu Thr Thr Asp Lys Val Ile His Asn
    50                  55              60

Ser Met Cys Ile Ala Glu Ile Asp Leu Ile Pro Arg Asp Arg Pro Phe
65                  70                  75                  80

Val Cys Ala Pro Ser Ser Lys Thr Gly Ala Val Thr Tyr Cys Cys Asn
                85                  90                  95

Gln Asp His Cys Asn Lys Ile Glu Leu Pro Thr Thr Gly Pro Phe Ser
            100                 105                 110

Glu Lys Gln Ser Ala Gly Leu Gly Pro Val Glu Leu Ala Ala Val Ile
        115                 120                 125

Ala Gly Pro Val Cys Phe Val Cys Ile Ala Leu Met Leu Met Val Tyr
    130                 135                 140

Ile Cys His Asn Arg Thr Val Ile His His Arg Val Pro Asn Glu Glu
145                 150                 155                 160

Asp Pro Ser Leu Asp Arg Pro Phe Ile Ser Glu Gly Thr Thr Leu Lys
                165                 170                 175

Asp Leu Ile Tyr Asp Met Thr Thr Ser Gly Ser Gly Ser Gly Leu Pro
            180                 185                 190

Leu Leu Val Gln Arg Thr Ile Ala Arg Thr Ile Val Leu Gln Glu Ser
        195                 200                 205

Ile Gly Lys Gly Arg Phe Gly Glu Val Trp Arg Gly Lys Trp Arg Gly
    210                 215                 220

Glu Glu Val Ala Val Lys Ile Phe Ser Ser Arg Glu Glu Arg Ser Trp
225                 230                 235                 240

Phe Arg Glu Ala Glu Ile Tyr Gln Thr Val Met Leu Arg His Glu Asn
                245                 250                 255

Ile Leu Gly Phe Ile Ala Ala Asp Asn Lys Asp Asn Gly Thr Trp Thr
            260                 265                 270

Gln Leu Trp Leu Val Ser Asp Tyr His Glu His Gly Ser Leu Phe Asp
        275                 280                 285

Tyr Leu Asn Arg Tyr Thr Val Thr Val Glu Gly Met Ile Lys Leu Ala
    290                 295                 300

Leu Ser Thr Ala Ser Gly Leu Ala His Leu His Met Glu Ile Val Gly

```
305                       310                       315                       320
Thr Gln Gly Lys Pro Ala Ile Ala His Arg Asp Leu Lys Ser Lys Asn
                325                     330                     335
Ile Leu Val Lys Lys Asn Gly Thr Cys Cys Ile Ala Asp Leu Gly Leu
            340                     345                     350
Ala Val Arg His Asp Ser Ala Thr Asp Thr Ile Asp Ile Ala Pro Asn
            355                     360                     365
His Arg Val Gly Thr Lys Arg Tyr Met Ala Pro Glu Val Leu Asp Asp
    370                     375                     380
Ser Ile Asn Met Lys His Phe Glu Ser Phe Lys Arg Ala Asp Ile Tyr
385                     390                     395                     400
Ala Met Gly Leu Val Phe Trp Glu Ile Ala Arg Arg Cys Ser Ile Gly
            405                     410                     415
Gly Ile His Glu Asp Tyr Gln Leu Pro Tyr Tyr Asp Leu Val Pro Ser
            420                     425                     430
Asp Pro Ser Val Glu Glu Met Arg Lys Val Val Cys Glu Gln Lys Leu
            435                     440                     445
Arg Pro Asn Ile Pro Asn Arg Trp Gln Ser Cys Glu Ala Leu Arg Val
    450                     455                     460
Met Ala Lys Ile Met Arg Glu Cys Trp Tyr Ala Asn Gly Ala Ala Arg
465                     470                     475                     480
Leu Thr Ala Leu Arg Ile Lys Lys Thr Leu Ser Gln Leu Ser Gln Gln
            48.5                    490                     495
Glu Gly Ile Lys Met
            500
```